(12) United States Patent
LaVon et al.

(10) Patent No.: US 8,585,672 B2
(45) Date of Patent: Nov. 19, 2013

(54) DISPOSABLE ABSORBENT ARTICLE HAVING DEPLOYABLE BELT EARS

(75) Inventors: Gary Dean LaVon, Liberty Township, OH (US); Kevin Michael Smith, Cincinnati, OH (US); Yoichiro Yamamoto, Cologne (DE); Michael Patrick Hayden, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 58 days.

(21) Appl. No.: 11/713,906

(22) Filed: Feb. 28, 2007

(65) Prior Publication Data

US 2008/0208156 A1    Aug. 28, 2008

(51) Int. Cl.
*A61F 13/15* (2006.01)

(52) U.S. Cl.
USPC .................. 604/392; 604/385.28; 604/385.11

(58) Field of Classification Search
USPC .......................... 604/385.11, 391–392, 385.28
See application file for complete search history.

(56) References Cited

U.S. PATENT DOCUMENTS

| | | | |
|---|---|---|---|
| 1,733,997 A | 10/1929 | Marr | |
| 1,734,499 A | 11/1929 | Marinsky | |
| 1,989,283 A | 1/1935 | Limacher | |
| 2,058,509 A | 10/1936 | Rose | |
| 2,271,676 A | 2/1942 | Bjornbak | |
| 2,450,789 A | 10/1948 | Frieman | |
| 2,508,811 A | 5/1950 | Best et al. | |
| 2,568,910 A | 9/1951 | Condylis | |
| 2,570,796 A | 10/1951 | Gross | |
| 2,570,963 A | 10/1951 | Mesmer | |
| 2,583,553 A | 1/1952 | Faure | |
| 2,705,957 A | 4/1955 | Mauro | |
| 2,788,786 A | 4/1957 | Dexter | |
| 2,798,489 A | 7/1957 | Behrman | |
| 2,807,263 A | 9/1957 | Newton | |
| 2,830,589 A | 4/1958 | Doner | |
| 2,890,700 A | 6/1959 | Lönberg-Holm | |
| 2,890,701 A | 6/1959 | Weinman | |
| 2,898,912 A | 8/1959 | Adams | |
| 2,931,361 A | 4/1960 | Sostsrin | |

(Continued)

FOREIGN PATENT DOCUMENTS

DE    1973-2499 C2    5/2001
EP    0 206 208    12/1986

(Continued)

OTHER PUBLICATIONS

International Search Report, Jan. 10, 2008.

*Primary Examiner* — Lynne Anderson
(74) *Attorney, Agent, or Firm* — Richard L. Alexander

(57) ABSTRACT

A simple disposable absorbent article including a chassis and an absorbent assembly. The chassis includes laterally opposing side flaps formed by laterally inwardly disposed portions of the chassis and deployable belt ears. Each belt ear is held laterally inwardly disposed until being released and deployed laterally outward so as to project laterally outward beyond the adjacent side flap. Fastening elements may be disposed on at least two of the belt ears, the fastening elements being adapted for fastening portions of the article together to encircle a waist and legs of a wearer. The chassis may be extensible. The absorbent assembly may be attached in a cruciform pattern to the chassis to allow portions of the chassis underlying the absorbent assembly and lying outside the cruciform attachment pattern to extend laterally.

19 Claims, 19 Drawing Sheets

(56) References Cited

U.S. PATENT DOCUMENTS

| | | |
|---|---|---|
| 2,977,957 A | 4/1961 | Clyne |
| 3,207,158 A | 9/1965 | Yoshitake et al. |
| 3,386,442 A | 6/1968 | Sabee |
| 3,561,446 A | 2/1971 | Jones |
| 3,572,342 A | 3/1971 | Lindquist et al. |
| 3,578,155 A | 5/1971 | Small et al. |
| 3,592,194 A | 7/1971 | Duncan |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,800,796 A | 4/1974 | Jacob |
| 3,814,100 A | 6/1974 | Nystrand et al. |
| 3,828,784 A | 8/1974 | Zoephel |
| 3,840,418 A | 10/1974 | Sabee |
| 3,847,702 A | 11/1974 | Jones |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,074,508 A | 2/1978 | Reid |
| 4,084,592 A | 4/1978 | Tritsch |
| 4,100,922 A | 7/1978 | Hernandez |
| 4,257,418 A | 3/1981 | Hessner |
| 4,296,750 A | 10/1981 | Woon et al. |
| 4,315,508 A | 2/1982 | Bolick |
| 4,324,246 A | 4/1982 | Mullane et al. |
| 4,342,314 A | 8/1982 | Radel et al. |
| 4,388,075 A | 6/1983 | Mesek et al. |
| 4,461,621 A | 7/1984 | Karami et al. |
| 4,463,045 A | 7/1984 | Ahr et al. |
| 4,475,912 A | 10/1984 | Coates |
| 4,490,148 A | 12/1984 | Beckeström |
| 4,585,450 A * | 4/1986 | Rosch et al. .................. 604/390 |
| 4,589,878 A | 5/1986 | Mitrani |
| 4,601,717 A | 7/1986 | Blevins |
| 4,610,678 A | 9/1986 | Weisman et al. |
| 4,636,207 A | 1/1987 | Buell |
| 4,670,011 A | 6/1987 | Mesek |
| 4,670,012 A | 6/1987 | Johnson |
| 4,680,030 A | 7/1987 | Coates et al. |
| 4,681,581 A | 7/1987 | Coates |
| 4,690,463 A | 9/1987 | Hart |
| 4,690,680 A * | 9/1987 | Higgins ........................ 604/386 |
| 4,695,278 A | 9/1987 | Lawson |
| 4,704,115 A | 11/1987 | Buell |
| 4,704,116 A | 11/1987 | Enloe |
| 4,731,066 A | 3/1988 | Korpman |
| 4,747,846 A | 5/1988 | Boland et al. |
| 4,787,896 A | 11/1988 | Houghton et al. |
| 4,795,454 A | 1/1989 | Dragoo |
| 4,802,884 A | 2/1989 | Fröidh et al. |
| 4,808,176 A | 2/1989 | Kielpikowski |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,846,825 A | 7/1989 | Enloe et al. |
| 4,861,652 A | 8/1989 | Lippert et al. |
| 4,888,231 A | 12/1989 | Angstadt |
| 4,892,528 A | 1/1990 | Suzuki et al. |
| 4,892,536 A | 1/1990 | DesMarais et al. |
| 4,904,251 A * | 2/1990 | Igaue et al. ............... 604/385.26 |
| 4,909,802 A * | 3/1990 | Ahr et al. .................... 604/385.3 |
| 4,909,803 A | 3/1990 | Aziz et al. |
| 4,940,463 A | 7/1990 | Leathers et al. |
| 4,940,464 A | 7/1990 | Van Gompel et al. |
| 4,950,264 A | 8/1990 | Osborn |
| 4,963,140 A | 10/1990 | Robertson et al. |
| 4,968,313 A | 11/1990 | Sabee |
| 4,990,147 A | 2/1991 | Freeland |
| 5,006,394 A | 4/1991 | Baird |
| 5,037,416 A | 8/1991 | Allen et al. |
| 5,071,414 A | 12/1991 | Elliott |
| 5,085,654 A | 2/1992 | Buell |
| 5,092,861 A | 3/1992 | Nomura et al. |
| 5,114,420 A | 5/1992 | Igaue et al. |
| 5,135,522 A | 8/1992 | Fahrenkrug et al. |
| D329,697 S | 9/1992 | Fahrenkrug et al. |
| 5,151,092 A | 9/1992 | Buell et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,246,431 A | 9/1993 | Minetola et al. |
| 5,246,432 A | 9/1993 | Suzuki et al. |
| 5,246,433 A | 9/1993 | Hasse et al. |
| 5,260,345 A | 11/1993 | Desmarais et al. |
| 5,269,775 A | 12/1993 | Freeland et al. |
| 5,312,386 A | 5/1994 | Correa et al. |
| 5,358,500 A | 10/1994 | LaVon et al. |
| 5,366,782 A | 11/1994 | Curro et al. |
| 5,387,209 A | 2/1995 | Yamamoto et al. |
| 5,397,316 A | 3/1995 | LaVon et al. |
| H1440 H | 5/1995 | New et al. |
| 5,476,458 A | 12/1995 | Glaug et al. |
| 5,518,801 A | 5/1996 | Chappell et al. |
| 5,531,730 A | 7/1996 | Dreier |
| 5,542,943 A | 8/1996 | Sageser |
| 5,549,592 A | 8/1996 | Fries et al. |
| 5,549,593 A | 8/1996 | Ygge et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,584,829 A | 12/1996 | Lavash et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,622,589 A | 4/1997 | Johnson et al. |
| 5,624,424 A | 4/1997 | Saisaka et al. |
| 5,625,222 A | 4/1997 | Yoneda et al. |
| 5,626,571 A | 5/1997 | Young et al. |
| 5,635,191 A | 6/1997 | Roe et al. |
| 5,643,243 A | 7/1997 | Klemp |
| 5,643,588 A | 7/1997 | Roe et al. |
| H1674 H | 8/1997 | Ames et al. |
| 5,662,638 A | 9/1997 | Johnson et al. |
| 5,674,215 A | 10/1997 | Ronnberg |
| 5,691,035 A | 11/1997 | Chappell et al. |
| 5,723,087 A | 3/1998 | Chappell et al. |
| 5,749,866 A * | 5/1998 | Roe et al. ................. 604/385.24 |
| 5,752,947 A | 5/1998 | Awolin |
| 5,772,825 A | 6/1998 | Schmitz |
| 5,776,121 A | 7/1998 | Roe et al. |
| 5,779,831 A | 7/1998 | Schmitz |
| 5,797,894 A | 8/1998 | Cadieux et al. |
| 5,810,800 A | 9/1998 | Hunter et al. |

(56) References Cited

U.S. PATENT DOCUMENTS

| | | | |
|---|---|---|---|
| 5,814,035 A | 9/1998 | Gryskiewicz et al. | |
| 5,846,232 A | 12/1998 | Serbiak et al. | |
| 5,851,204 A | 12/1998 | Mitzutani | |
| 5,853,402 A | 12/1998 | Faulks et al. | |
| 5,865,823 A | 2/1999 | Curro | |
| 5,873,868 A | 2/1999 | Nakahata | |
| 5,876,391 A | 3/1999 | Roe et al. | |
| 5,891,544 A | 4/1999 | Chappell et al. | |
| 5,897,545 A | 4/1999 | Kline et al. | |
| 5,904,673 A | 5/1999 | Roe et al. | |
| 5,931,825 A | 8/1999 | Kuen et al. | |
| 5,951,536 A | 9/1999 | Osborn, III et al. | |
| 5,957,908 A | 9/1999 | Kline et al. | |
| 5,968,029 A | 10/1999 | Chappell et al. | |
| 6,004,306 A | 12/1999 | Robles et al. | |
| 6,022,430 A | 2/2000 | Blenke et al. | |
| 6,022,431 A | 2/2000 | Blenke et al. | |
| 6,042,673 A | 3/2000 | Johnson et al. | |
| 6,102,892 A | 8/2000 | Putzer et al. | |
| 6,107,537 A | 8/2000 | Elder et al. | |
| 6,110,157 A * | 8/2000 | Schmidt | 604/385.01 |
| 6,117,121 A | 9/2000 | Faulks et al. | |
| 6,117,803 A | 9/2000 | Morman et al. | |
| 6,120,486 A | 9/2000 | Toyoda et al. | |
| 6,120,487 A | 9/2000 | Ashton | |
| 6,120,489 A | 9/2000 | Johnson et al. | |
| 6,120,866 A | 9/2000 | Arakawa et al. | |
| 6,129,720 A | 10/2000 | Blenke et al. | |
| 6,156,424 A | 12/2000 | Taylor | |
| 6,165,160 A | 12/2000 | Suzuki et al. | |
| 6,174,302 B1 | 1/2001 | Kumasaka | |
| 6,177,607 B1 | 1/2001 | Blaney et al. | |
| 6,186,996 B1 | 2/2001 | Martin | |
| 6,210,390 B1 | 4/2001 | Karlsson | |
| 6,238,380 B1 | 5/2001 | Sasaki | |
| 6,241,716 B1 | 6/2001 | Rönnberg et al. | |
| 6,312,420 B1 | 11/2001 | Sasaki et al. | |
| 6,322,552 B1 | 11/2001 | Blenke et al. | |
| 6,325,787 B1 | 12/2001 | Roe et al. | |
| 6,334,858 B1 | 1/2002 | Rönnberg et al. | |
| 6,350,332 B1 | 2/2002 | Thomas et al. | |
| 6,364,863 B1 | 4/2002 | Yamamoto et al. | |
| 6,402,729 B1 | 6/2002 | Boberg et al. | |
| 6,402,731 B1 | 6/2002 | Suprise et al. | |
| 6,410,820 B1 | 6/2002 | McFall et al. | |
| 6,413,249 B1 | 7/2002 | Turi et al. | |
| 6,419,667 B1 | 7/2002 | Avalon et al. | |
| 6,432,098 B1 | 8/2002 | Kline et al. | |
| 6,432,099 B2 | 8/2002 | Rönnberg | |
| 6,443,933 B1 | 9/2002 | Suzuki et al. | |
| 6,461,342 B2 | 10/2002 | Tanji et al. | |
| 6,461,343 B1 | 10/2002 | Schaefer et al. | |
| 6,475,201 B2 | 11/2002 | Saito et al. | |
| 6,494,872 B1 | 12/2002 | Suzuki et al. | |
| 6,494,873 B2 | 12/2002 | Karlsson et al. | |
| 6,520,947 B1 | 2/2003 | Tilly et al. | |
| 6,524,294 B1 | 2/2003 | Hilston et al. | |
| 6,572,602 B2 * | 6/2003 | Furuya et al. | 604/391 |
| 6,585,713 B1 | 7/2003 | LaMahieu et al. | |
| 6,602,234 B2 | 8/2003 | Klemp et al. | |
| 6,605,070 B2 | 8/2003 | Ludwig et al. | |
| 6,626,881 B2 | 9/2003 | Shingu et al. | |
| 6,648,869 B1 | 11/2003 | Gillies et al. | |
| 6,648,870 B1 | 11/2003 | Itoh et al. | |
| 6,648,871 B2 | 11/2003 | Kusibojoska et al. | |
| 6,652,696 B2 | 11/2003 | Kuen et al. | |
| 6,682,515 B1 | 1/2004 | Mizutani et al. | |
| 6,689,115 B1 | 2/2004 | Popp et al. | |
| 6,716,205 B2 | 4/2004 | Popp et al. | |
| 6,726,792 B1 | 4/2004 | Johnson et al. | |
| 6,730,070 B2 * | 5/2004 | Holmquist | 604/392 |
| 6,755,808 B2 | 6/2004 | Balogh et al. | |
| 6,818,083 B2 | 11/2004 | Mcamish et al. | |
| 6,878,223 B2 | 4/2005 | Kuen et al. | |
| 6,880,211 B2 | 4/2005 | Jackson et al. | |
| 6,923,797 B2 | 8/2005 | Shinohara et al. | |
| 6,962,578 B1 | 11/2005 | LaVon | |
| 6,972,010 B2 | 12/2005 | Pesce et al. | |
| 7,014,632 B2 | 3/2006 | Takino et al. | |
| 7,037,299 B2 | 5/2006 | Turi et al. | |
| 7,048,726 B2 | 5/2006 | Kusagawa et al. | |
| 7,112,193 B2 | 9/2006 | Otsubo | |
| 7,320,684 B2 * | 1/2008 | LaVon et al. | 604/392 |
| 2001/0041879 A1 * | 11/2001 | Karami et al. | 604/386 |
| 2002/0045881 A1 | 4/2002 | Kusibojoska et al. | |
| 2002/0099351 A1 | 7/2002 | Onishi et al. | |
| 2002/0173767 A1 | 11/2002 | Popp et al. | |
| 2002/0193776 A1 * | 12/2002 | Fernfors | 604/389 |
| 2003/0088223 A1 | 5/2003 | Vogt et al. | |
| 2003/0144644 A1 | 7/2003 | Murai et al. | |
| 2003/0148694 A1 | 8/2003 | Ghiam | |
| 2003/0233082 A1 | 12/2003 | Kline et al. | |
| 2004/0022998 A1 | 2/2004 | Miyamoto et al. | |
| 2004/0082928 A1 | 4/2004 | Pesce et al. | |
| 2004/0122411 A1 | 6/2004 | Hancock-Cooke | |
| 2004/0147890 A1 | 7/2004 | Nakahata et al. | |
| 2004/0162536 A1 | 8/2004 | Becker et al. | |
| 2004/0167486 A1 | 8/2004 | Busam et al. | |
| 2004/0225271 A1 | 11/2004 | Datta et al. | |
| 2004/0236299 A1 | 11/2004 | Tsang et al. | |
| 2004/0236304 A1 | 11/2004 | Coates et al. | |
| 2004/0249355 A1 | 12/2004 | Tanio et al. | |
| 2005/0004548 A1 | 1/2005 | Otsubo et al. | |
| 2005/0038401 A1 | 2/2005 | Suzuki et al. | |
| 2005/0085784 A1 | 4/2005 | LeMinh et al. | |
| 2005/0131373 A1 | 6/2005 | Wright et al. | |
| 2005/0171499 A1 | 8/2005 | Nigam et al. | |
| 2005/0203475 A1 | 9/2005 | LaVon et al. | |
| 2005/0203479 A1 | 9/2005 | Sakaguchi et al. | |
| 2005/0288645 A1 | 12/2005 | LaVon | |
| 2005/0288646 A1 | 12/2005 | LaVon | |
| 2006/0264860 A1 | 11/2006 | Beck | |
| 2007/0049897 A1 | 3/2007 | LaVon et al. | |
| 2007/0066951 A1 | 3/2007 | LaVon et al. | |
| 2007/0066952 A1 | 3/2007 | LaVon et al. | |
| 2007/0118091 A1 | 5/2007 | LaVon et al. | |

FOREIGN PATENT DOCUMENTS

| | | |
|---|---|---|
| EP | 0 403 832 A1 | 12/1990 |
| EP | 374542 B1 | 11/1994 |
| EP | 0 893 115 | 1/1999 |
| EP | 0 916 327 A1 | 5/1999 |
| EP | 1 110 529 | 6/2001 |
| EP | 761194 B1 | 12/2001 |
| EP | 793469 B1 | 6/2002 |
| EP | 1447066 A1 | 8/2004 |
| EP | 951890 B1 | 1/2006 |
| EP | 1224922 B1 | 4/2007 |
| EP | 1447067 B1 | 12/2007 |
| ES | 2 213 491 A1 | 8/2004 |
| FR | 2 566 631 A1 | 1/1986 |
| FR | 2 612 770 A1 | 9/1988 |
| FR | 2 810 234 | 12/2001 |
| GB | 1307441 A | 2/1973 |
| GB | 1 513 055 | 6/1978 |
| GB | 2 101 468 | 1/1983 |
| GB | 2 262 873 A | 7/1993 |
| JP | 04 122256 | 4/1992 |
| JP | 11-318980 | 11/1999 |
| WO | WO-84-04242 | 11/1984 |
| WO | WO 95/16746 A1 | 6/1995 |
| WO | WO 95/29657 | 11/1995 |
| WO | WO 98/16179 A1 | 4/1998 |
| WO | WO 99/13813 | 3/1999 |
| WO | WO-03-009794 A9 | 4/2004 |
| WO | WO 2004/105664 | 12/2004 |
| WO | WO 2007/000315 | 1/2007 |
| WO | WO-2007-034348 A1 | 3/2007 |

* cited by examiner

DISPOSABLE ABSORBENT ARTICLE HAVING DEPLOYABLE BELT EARS

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact.

As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

The present invention provides a simple disposable absorbent article including a chassis and an absorbent assembly. The chassis includes laterally opposing side flaps formed by laterally inwardly folded portions of the chassis and deployable belt ears. Each belt ear is held laterally inwardly disposed until being released and deployed laterally outward so as to project laterally outward beyond the adjacent side flap. Fastening elements may be disposed on at least two of the belt ears, the fastening elements being adapted for fastening portions of the article together to encircle a waist and legs of a wearer. The absorbent assembly may be attached in a cruciform pattern to the chassis to allow portions of the chassis underlying the absorbent assembly and lying outside the cruciform attachment pattern to extend laterally.

BRIEF DESCRIPTION OF THE DRAWINGS

In the accompanying drawing figures, like reference numerals identify structurally corresponding elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In the drawing figures and in the written description, lowercase letters appended to reference numerals indicate generally symmetric elements, e.g., left and right symmetric elements may be respectively identified by the reference numerals 1*a* and 1*b*. A reference numeral without an appended lowercase letter identifies all of the elements to which that particular reference numeral applies, e.g., the same elements as a group may be designated 1.

DETAILED DESCRIPTION OF THE INVENTION

Figure 1:
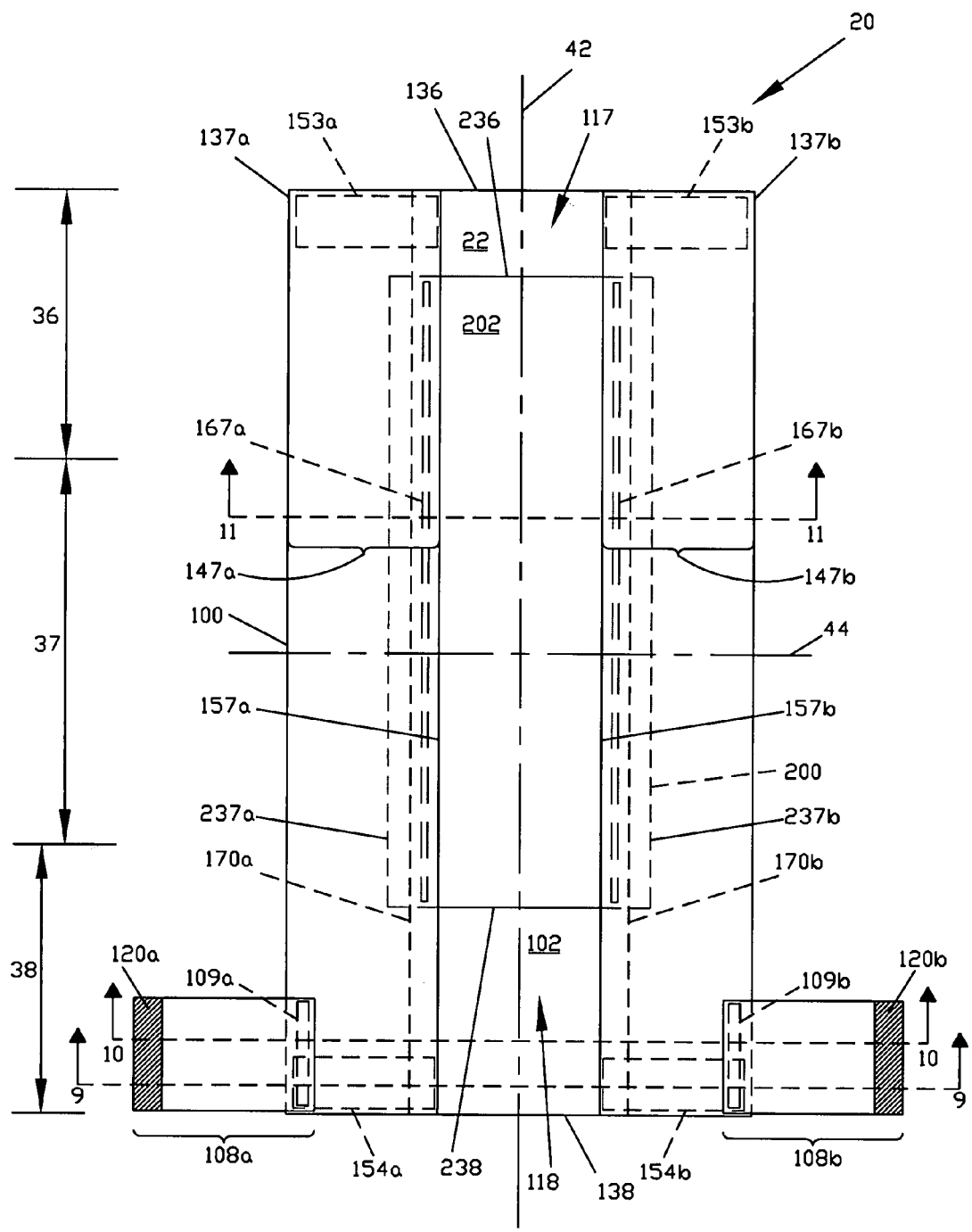
FIG. 1 is a plan view of an exemplary disposable absorbent article in the form of a diaper 20, which is shown in its flat, uncontracted state, i.e., without the contraction induced by elastic members. In this figure, the interior portion of the diaper 20 that faces inwardly toward the wearer and contacts the wearer is shown facing the viewer.

In this description, the following terms have the following meanings:

The term "absorbent article" refers to a device that absorbs and contains liquid, and more specifically, refers to a device that is placed against or in proximity to the body of a wearer to absorb and contain the various exudates discharged from the body.

The term "diaper" refers to an absorbent article that is generally worn by infants and incontinent persons about the lower torso so as to encircle the waist and the legs of the wearer and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner. In this description, a disposable diaper is described as being representative of an exemplary disposable absorbent article.

The term "deploy" in all its forms refers to the manipulation of any disclosed deployable structural element from its initial configuration to a configuration in which it can be used for its intended purpose in the article on which it is provided.

The term "longitudinal" refers to a direction running from a waist edge to an opposing waist edge of the article and generally parallel to the maximum linear dimension of the article.

The term "lateral" refers to a direction running from a side edge to an opposing side edge of the article and generally at a right angle to the longitudinal direction.

The term "diagonal" refers to an orientation of a line extending obliquely relative to the longitudinal and lateral directions, i.e., neither perpendicular nor parallel to either of the longitudinal or lateral directions.

The term "circumferential" refers to a direction generally encircling the waist of the wearer parallel to the lateral direction. This term is used particularly when describing the elements that extend around and form the margin of the waist opening.

The term "disposed" refers to an element being attached and positioned in a particular place or position in a unitary structure with other elements.

The term "attach" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, etc. Such attachment methods may be used to attach elements together over a particular area either continuously or intermittently. Unless indicated otherwise, elements that are described as being attached to each other are attached directly together, with either nothing or only bonding material, e.g., an adhesive, between them. Unless indicated otherwise, elements that are described as being attached to each other are attached permanently together, i.e., attached in such a way that one or both of the elements and/or any bonding material that is present must be damaged in order to separate them. This permanent attachment excludes temporary attachment, such as fastening elements together by means of fasteners that may be unfastened.

The term "laminate" refers to elements being attached together in a layered arrangement.

The term "cohesive" refers to the property of a material that, once set, sticks to itself but does not to any significant degree stick to other materials.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "proximal" and "distal" refer respectively to the location of an element relatively near to or far from the center of a structure, e.g., the laterally proximal edge of a longitudinally extending element is located nearer to the longitudinal axis than the laterally distal edge of the same element is located relative to the same longitudinal axis. When used to describe relative locations with respect to the axes, synonyms include "inboard" and "outboard", respectively.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower", "above" and "below", "over" and "under", and "top" and "bottom", respectively.

The term "nonwoven" refers to a sheet, web, or batt of directionally or randomly oriented fibers, made by bonding or entangling the fibers through mechanical, thermal, or chemical means. Nonwoven materials exclude paper and products which are woven, knitted, tufted, or felted by wet milling. The fibers are preferably but not necessarily man-made synthetics.

As can be seen in the drawing figures, one end portion of the exemplary diaper 20 is configured as a front waist region 36, the longitudinally opposing end portion is configured as a back waist region 38, and an intermediate portion is configured as a crotch region 37.

The basic structure of the diaper 20 includes a chassis 100, which has a laterally extending front edge 136, a longitudinally opposing back edge 138, laterally opposing side edges 137, an interior surface 102, and an exterior surface 104. A longitudinal axis 42 extends through the midpoints of the front edge 136 and the back edge 138 and a lateral axis 44 extends through the midpoints of the side edges 137. The exemplary chassis 100 shown in FIG. 1 additionally has longitudinally extending and laterally opposing side flaps 147 as well as laterally opposing belt ears 108, which are described in more detail below.

The basic structure of the diaper 20 also includes an absorbent assembly 200 that is attached to the chassis 100. The absorbent assembly 200 absorbs and retains liquid bodily waste materials. The absorbent assembly 200 has a laterally extending front edge 236, a longitudinally opposing back edge 238, laterally opposing side edges 237, an interior surface 202, and an exterior surface 204. The absorbent assembly 200 may be disposed either symmetrically or asymmetrically with respect to either or both of the longitudinal axis 42 and the lateral axis 44. For example, the absorbent assembly 200 shown in FIG. 1 is disposed symmetrically with respect to the longitudinal axis 42 and asymmetrically offset toward the front waist region 36 with respect to the lateral axis 44.

The edges of the absorbent assembly 200 may lie inward of the respective edges of the chassis 100, as in the exemplary diaper 20 shown in FIG. 1. Such a configuration in which one or more of the edges of the absorbent assembly 200 lies inward of the corresponding edges of the chassis 100 may be desirable, for example, in order to allow the relatively more flexible layer or layers adjacent to the edges of the chassis to conform to the body of the wearer and thereby form effective gasket-like seals against the skin of the wearer without being constrained by a relatively thicker and relatively less flexible absorbent assembly. Alternatively, one or more of the edges of the absorbent assembly 200 may coincide with the corresponding edge or edges of the chassis 100.

When the diaper 20 is worn on the lower torso of a wearer, the front waist edge 136 and the back waist edge 138 encircle the waist of the wearer at least partially, while at the same time the chassis side edges 137 encircle the legs of the wearer at least partially, the crotch region 37 is generally positioned between the legs of the wearer, and the absorbent assembly 200 extends from the front waist region 36 through the crotch region 37 to the back waist region 38.

Figure 23:
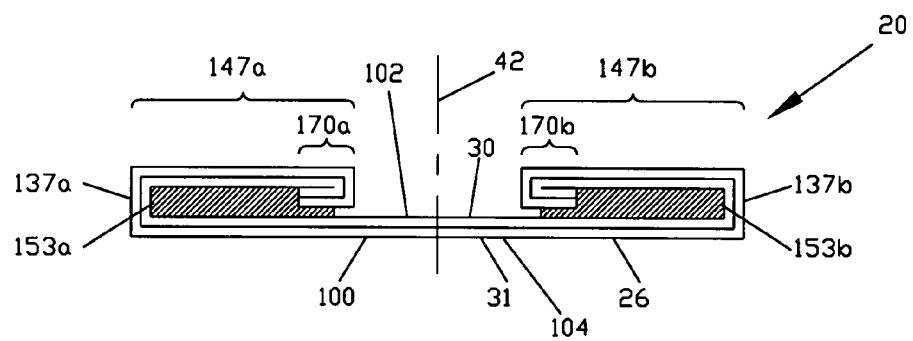
FIG. 23 is a section view of a diaper 20 showing details of the backsheet 26.
Figure 24:
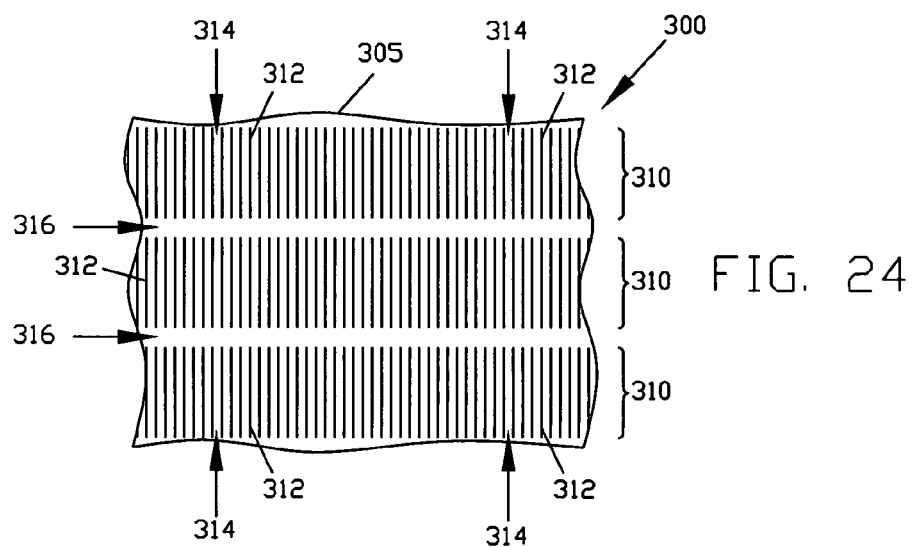
FIG. 24 is a plan view of an exemplary fragment of a formed web material.
Figure 25:
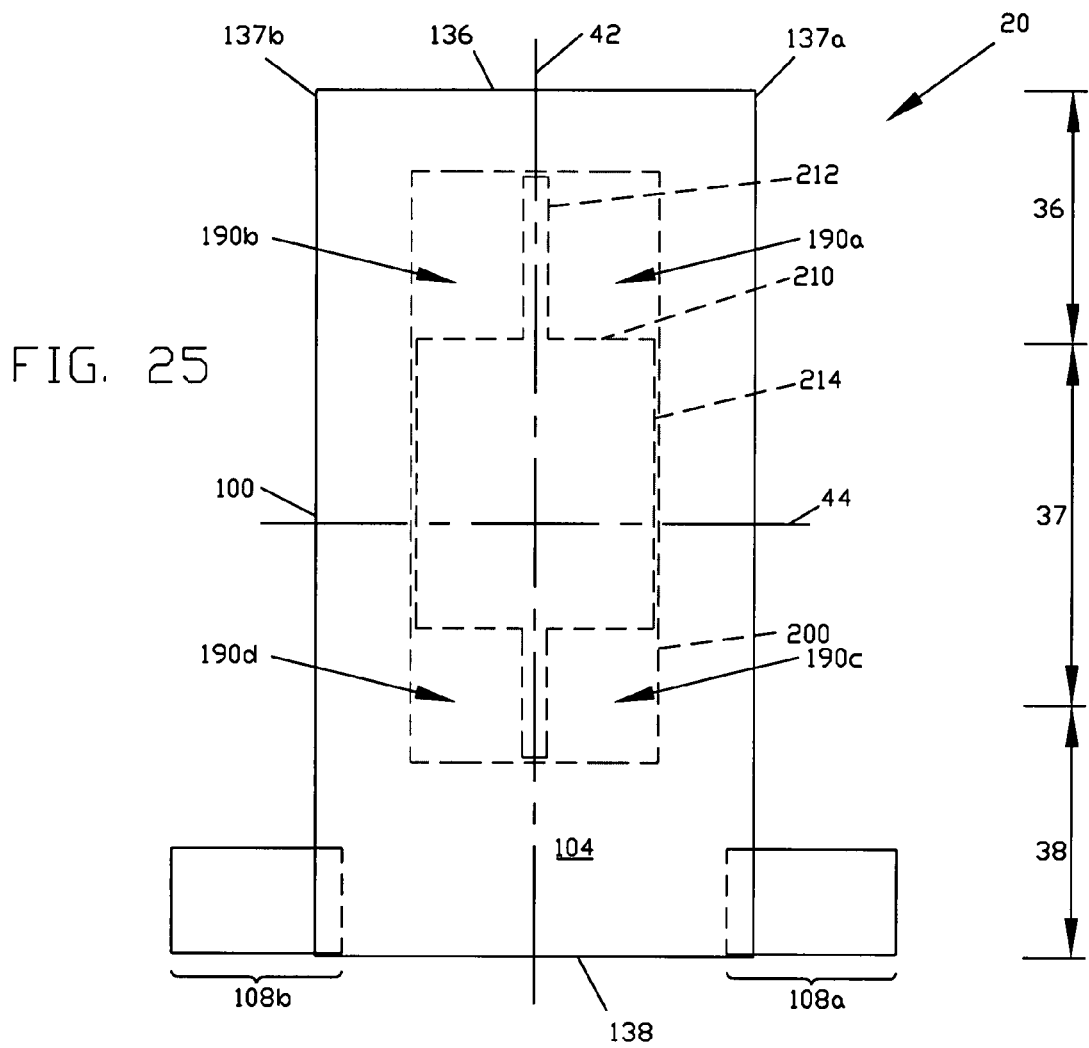
FIG. 25 is a simplified plan view of an exemplary diaper 20, which is shown in its flat, uncontracted state, i.e., without the contraction induced by elastic members, having the absorbent assembly attached to the chassis in a cruciform attachment pattern. In this figure, the exterior portion of the diaper 20 is shown facing the viewer.
Figure 26:
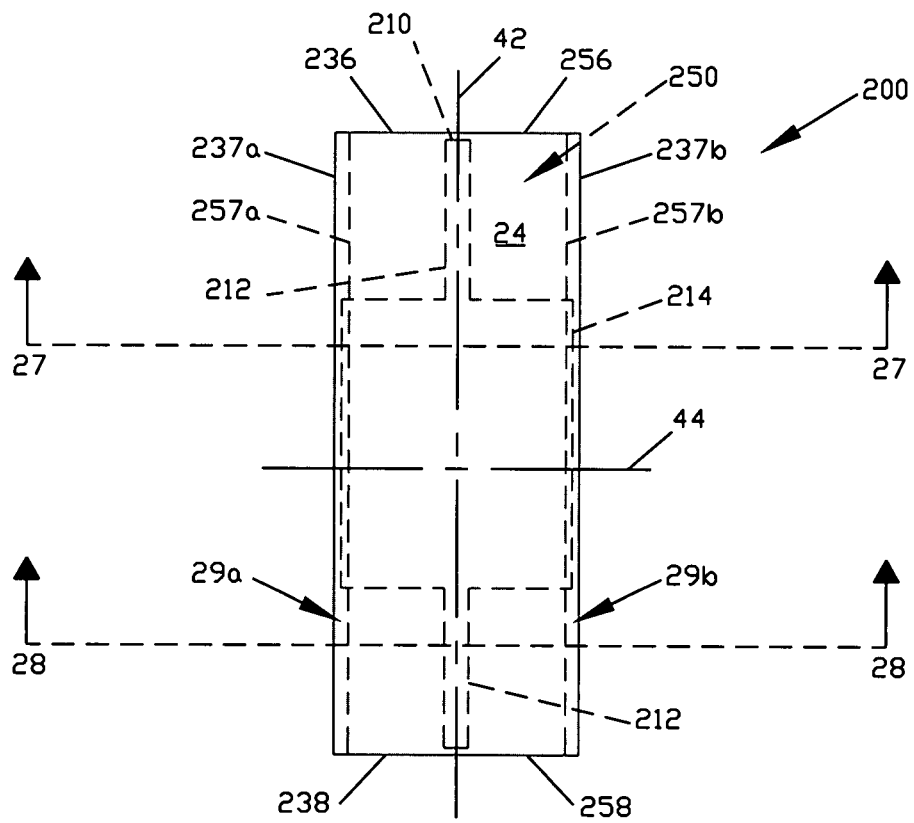
FIG. 26 is a plan view of an exemplary absorbent assembly 200. In this figure, the absorbent assembly 200 is shown separately from a chassis 100 to which it is attached in an exemplary diaper 20 and the interior portion of the absorbent assembly 200 that faces inwardly toward the wearer and contacts the wearer is shown facing the viewer.
Figure 27:
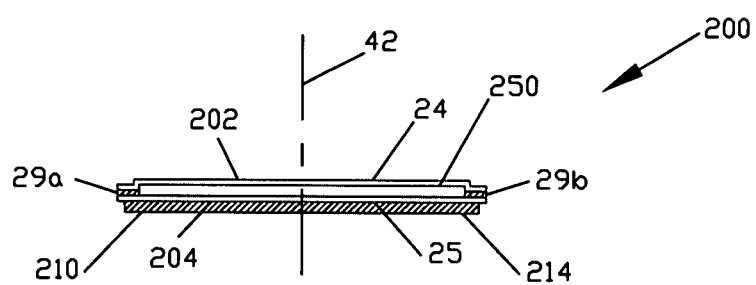
FIG. 27 is a section view of the absorbent assembly 200 of FIG. 26 taken at the section line 27-27.
Figure 28:
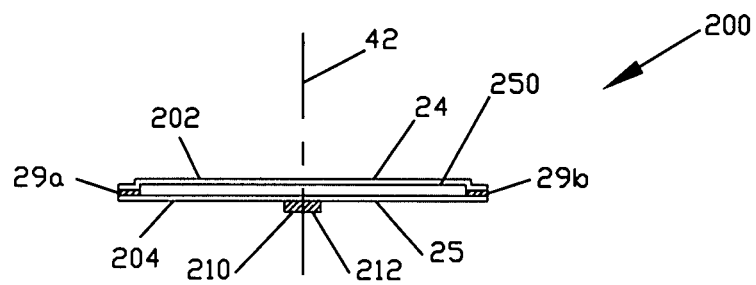
FIG. 28 is a section view of the absorbent assembly 200 of FIG. 26 taken at the section line 28-28.

The chassis 100 includes a water-impermeable backsheet 26. The backsheet 26 forms an exterior surface that is intended to be placed toward any clothing that is worn over the diaper 20. Many suitable materials for use as the backsheet 26 are well-known, including films of polyethylene and other polyolefins. Multi-layer backsheets, such as laminates of a film and a nonwoven, are also well-known and may be suitable for use as the backsheet 26. Such a laminate backsheet may be oriented with the nonwoven 31 disposed exteriorly, as shown in FIG. 23, to provide the feel and appearance of a more cloth-like outermost layer than would be provided by using the film 30 as the outermost layer.

The chassis 100 may, but need not, additionally include an inner liner 22 attached to the backsheet 26. Such an inner liner 22 preferably is formed of a soft material that will not irritate the skin of the wearer. Many suitable materials for the inner liner 22 are well-known in the art, including rayon and synthetic nonwovens such as spunbonded or carded polypropylene, polyethylene, or polyester. An inner liner 22 may form a portion of the interior surface 102 of the chassis 100, such as in the respective front and back laterally central portions 117 and 118 between the edges 236 and 238 of the absorbent assembly 200 and the waist edges 136 and 138 of the chassis 100 and thereby serve to isolate the skin of the wearer from a portion of the backsheet 26 as may be desirable, for example, when the diaper 20 is worn under conditions in which contact between the skin and a backsheet film could be uncomfortable.

Figure 31:
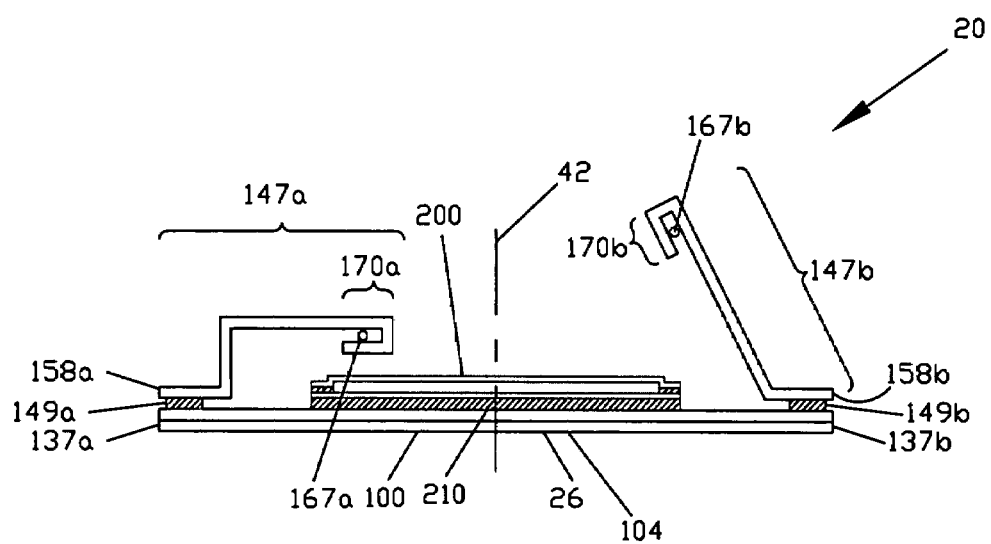
FIG. 31 is a section view of an alternative embodiment of the diaper 20 taken at a section line similar to 11-11 and showing an alternative construction of the side flaps 147.

As shown in the figures, the exemplary chassis 100 has longitudinally extending and laterally opposing side flaps 147 that are disposed on the interior portion of the diaper 20 that faces inwardly toward the wearer and contacts the wearer. The side flaps 147 may be formed by folding portions of the chassis 100 laterally inward, i.e., toward the longitudinal axis 42, to form both the respective side flaps 147 and the side edges 137 of the chassis 100. Alternatively, the side flaps 147 may be formed by attaching an additional layer or layers to the chassis 100 at or adjacent to each of the respective side edges 137 of the chassis 100. In embodiments in which the side flaps are formed by attaching an additional layer or layers to the chassis, each of the additional layer or layers may be attached in an attachment zone 149 at or adjacent to its laterally distal edge 158 as shown in FIG. 31.

In the exemplary diaper 20 shown in FIG. 1, the side flaps 147 overlap the absorbent assembly 200, i.e., their proximal edges 157 lie laterally inward of the respective side edges 237 of the absorbent assembly 200. Such an overlapped configuration may be desirable in order to impart a more finished appearance to the diaper 20 than that imparted by a non-overlapped configuration. Alternatively, the side flaps 147 may not overlap the absorbent assembly 200.

Each side flap 147 is attached to the interior surface 102 of the chassis 100 in an attachment zone 153 adjacent to the front waist edge 136 and in a longitudinally opposing attachment zone 154 adjacent to the back waist edge 138, as shown in the figures.

In embodiments in which the front edge 236 or the back edge 238 of the absorbent assembly 200 coincides with the respective front waist edge 136 or back waist edge 138 of the chassis 100 and the side flaps 147 overlap the absorbent assembly 200, the side flaps 147 may be attached to the absorbent assembly 200 instead of, or in addition to, being attached to the interior surface 102 of the chassis 100.

Figure 3:
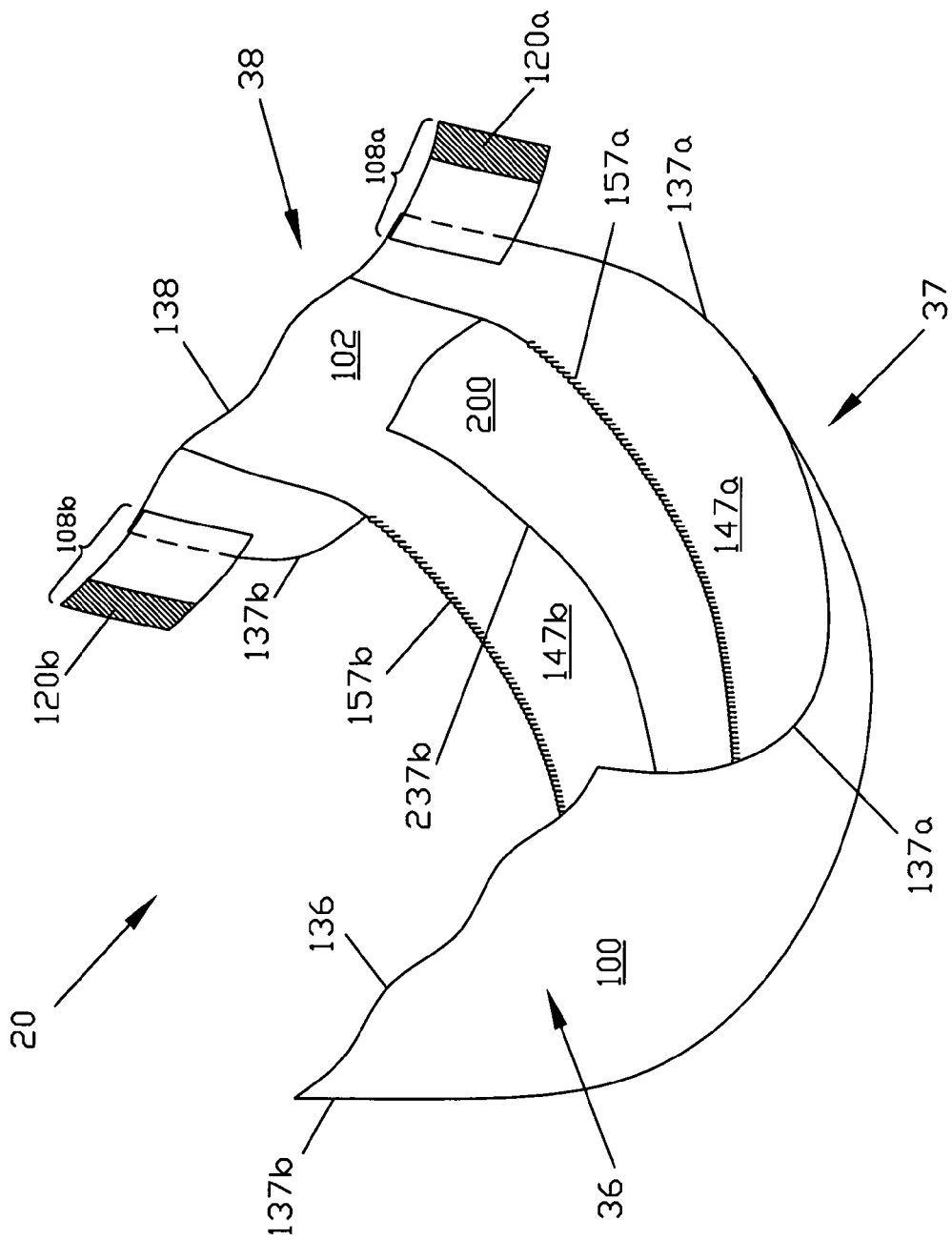
FIG. 3 is a perspective view of an exemplary diaper 20, which is shown in its relaxed, contracted state, i.e., with the contraction induced by elastic members. In this figure, the interior portion of the diaper 20 is shown facing upward.
Figure 11:
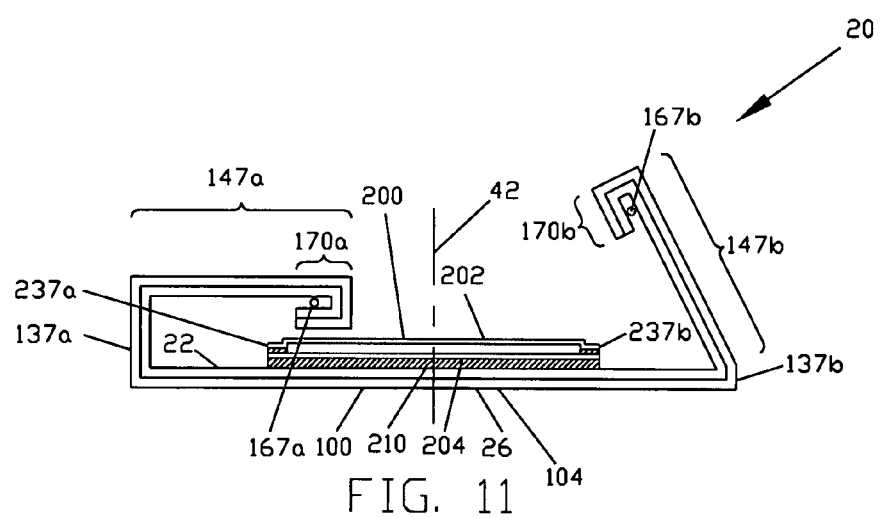
FIG. 11 is a section view of the diaper 20 of FIGS. 1 and 2 taken at the section line 11-11.

Between the attachment zones, the proximal edge 157 of the side flap 147 remains free, i.e., not attached to the interior surface 102 of the chassis 100 or to the absorbent assembly 200. Also between the attachment zones, an elastic strand 167 is attached adjacent to the proximal edge 157 of each side flap 147. Each elastic strand 167 is enclosed inside a hem 170 formed adjacent to the proximal edge 157 of each side flap 147. When stretched, the elastic strand 167 allows the adjacent side flap edge to extend to the flat uncontracted length of the chassis. When allowed to relax, the elastic strands 167 contract and lifts the proximal edges 157, thereby lifting the side flaps 147 into position to serve as side barriers adjacent to the side edges 237 of the absorbent assembly 200, as shown in FIG. 3 and FIG. 11.

A portion or the whole of the chassis 100 may be made extensible to a degree greater than the inherent extensibility of the material or materials from which the chassis is made, e.g., the backsheet 26. The additional extensibility may be desirable in order to allow the chassis 100 to conform to the body of a wearer during movement by the wearer. The additional extensibility may also be desirable, for example, in order to allow the user of a diaper 20 including a chassis 100 having a particular size before extension to extend the front waist region 36, the back waist region 38, or both waist regions of the chassis 100 to provide additional body coverage for wearers of differing size, i.e., to tailor the diaper to the individual wearer. Such extension of the waist region or regions may give the diaper a generally hourglass shape, so long as the crotch region 37 is extended to a relatively lesser degree than the waist region or regions, and may impart a tailored appearance to the diaper 20 when it is worn. In addition, the additional extensibility may be desirable in order to minimize the cost of the diaper. For example, an amount of material that would otherwise be sufficient only to make a relatively smaller diaper lacking this extensibility can be used to make a diaper capable of being extended to adequately cover a wearer that is larger than the unextended smaller diaper would fit.

Additional lateral extensibility in the chassis 100 may be provided in a variety of ways. For example, a material or materials from which the chassis 100 is made may be pleated by any of many known methods. Alternatively, all or a portion of the chassis may be made of a formed web material or a formed laminate of web materials like those described in U.S. Pat. No. 5,518,801 issued on 21 May 1996. This formed web material includes distinct laterally extending regions in which the original material has been altered by embossing or another method of deformation to create a pattern of generally longitudinally oriented alternating ridges and valleys and also includes laterally extending unaltered regions between the laterally extending altered regions. The formed web material can be extended in a direction perpendicular to the ridges up to the point where the ridges and valleys flatten with substantially less force than is required to extend beyond that point.

The front laterally central portion 117 and the back laterally central portion 118 of the chassis 100 may have a different range of extensibility from the portions of the chassis in the attachment zones where the side flaps 147 are attached. Additionally or alternatively, the laterally central portions 117 and 118 may be extensible to a greater or lesser degree when subjected to a given level of opposing tensile forces, i.e., may be more easily or less easily extensible, than the portions of the chassis in the attachment zones. For example, if the chassis is made uniformly extensible across its entire width prior to the formation of the side flaps, the double layering in the areas of the attachment zones after the formation of the side flaps may have an effect of decreasing the degree of lateral extensibility of those areas under a given level of opposing tensile forces, such as by the side flaps acting as parallel "springs" that must be extended in order to extend the underlying attached portion of the chassis. As another example, the altered regions in the laterally central portions of the chassis may be deformed to a greater or a lesser degree than the altered regions in the attachment zones to render the laterally central portions more easily or less easily extensible than the respective portions in the attachment zones.

In the finished diaper, it is preferable that the chassis not be rectangular, but instead have an overall shape in plan view of a "T" or of an "I". Such a non-rectangular configuration may impart a tailored appearance to the diaper 20 when it is worn and may also impart an impression that the diaper 20 will fit comfortably between the legs of a wearer.

Figure 2:
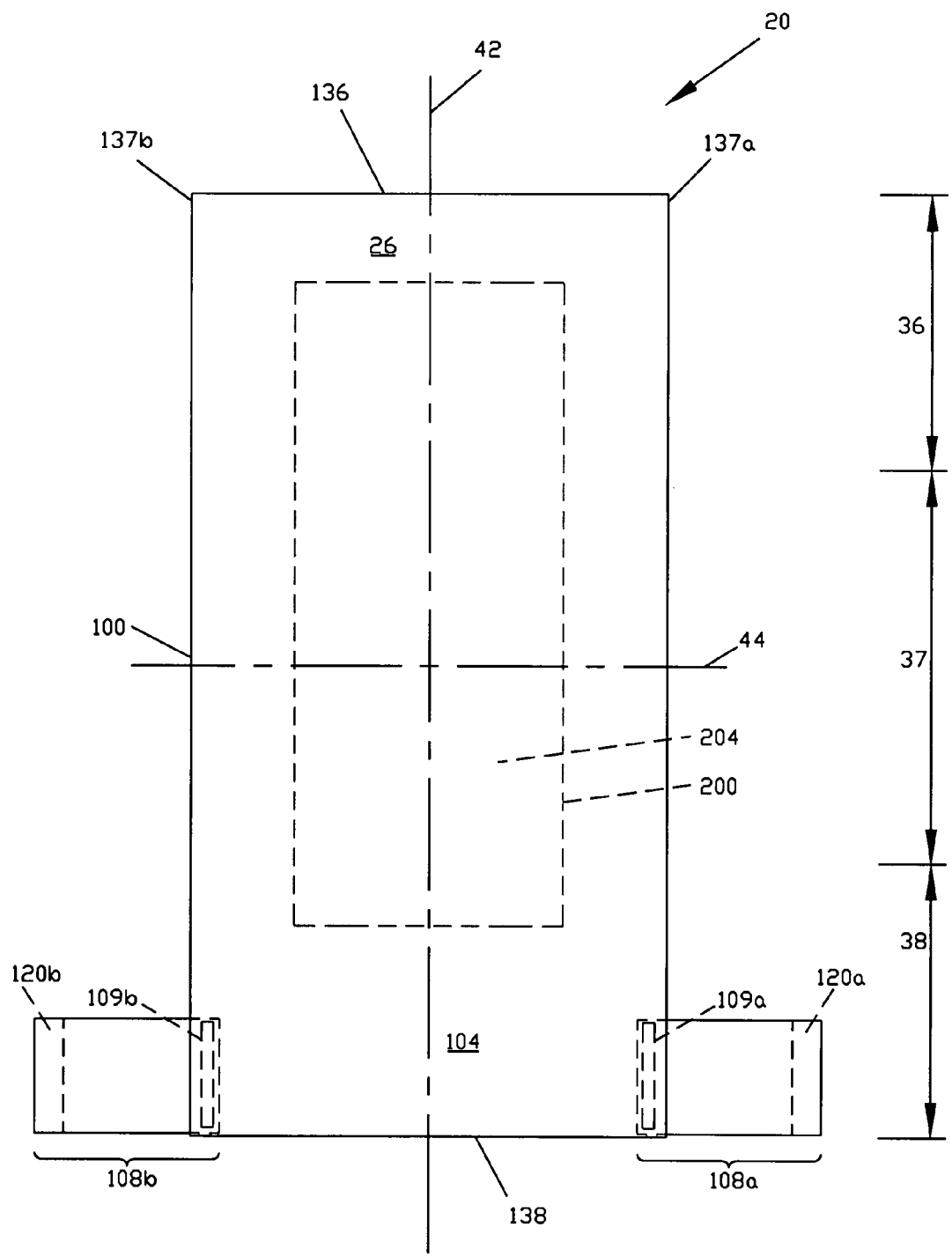
FIG. 2 is a plan view of the diaper 20 of FIG. 1 with the exterior portion of the diaper 20 shown facing the viewer.
Figure 4:
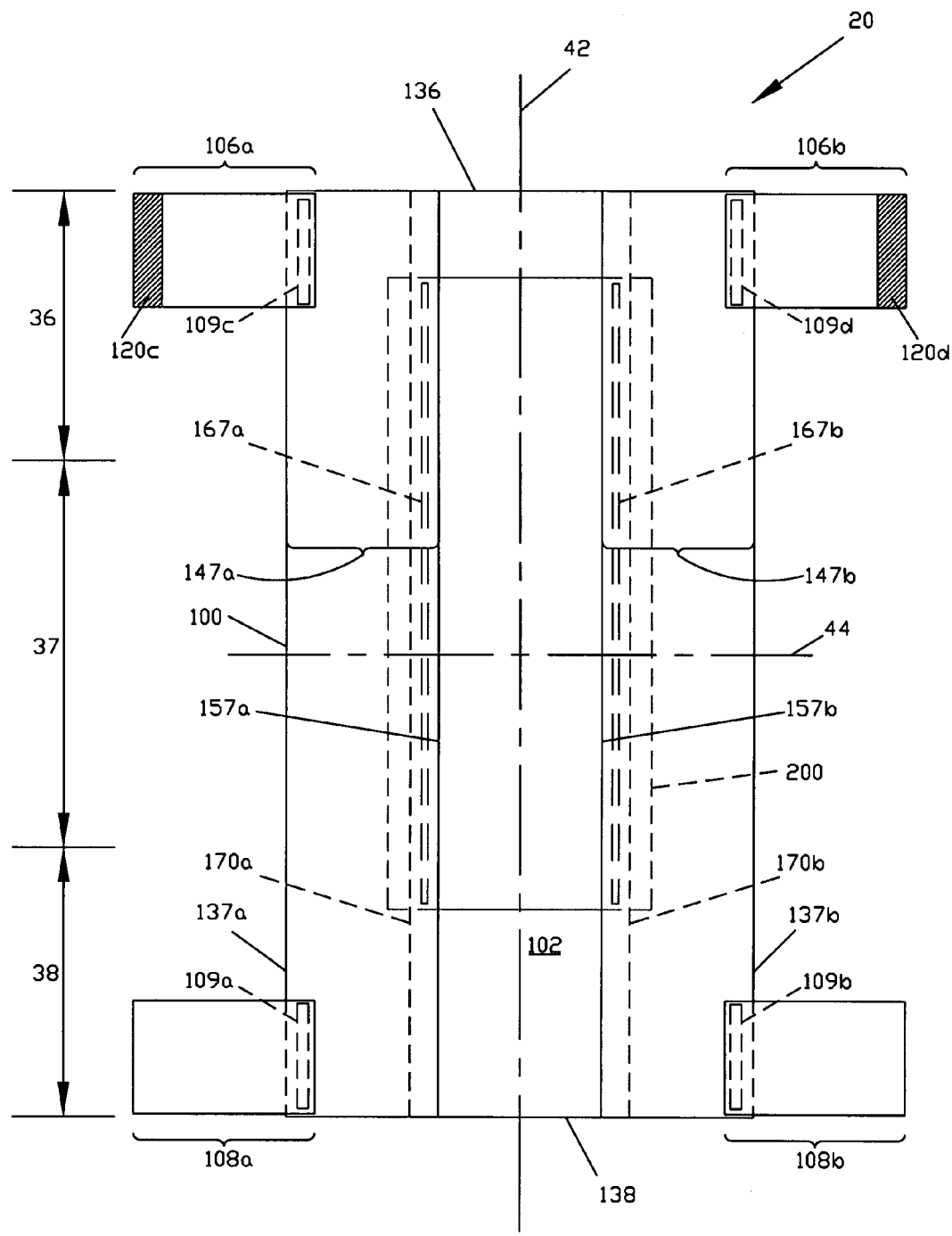
FIG. 4 is a plan view of another exemplary diaper 20 with four belt ears extending laterally. In this figure, the interior portion of the diaper 20 is shown facing the viewer.

An exemplary non-rectangular configuration of the chassis is shown in FIG. 1, FIG. 2, and FIG. 3. As shown in these figures, laterally opposing belt ears 108 in the back waist region 38 extend laterally outward while the adjacent side flaps 147 remain folded laterally inward. The laterally outwardly extending belt ears 108 impart a "T" shape to the diaper. Laterally opposing belt ears 106 in the front waist region 36 may similarly extend laterally outward to impart a "T" shape to the diaper. As shown in FIG. 4, in some exemplary embodiments, both front belt ears 106 and back belt ears 108 may extend laterally outward while the adjacent side flaps 147 remain folded laterally inward, in which configuration a "I" shape is imparted to the diaper 20.

Figure 5:
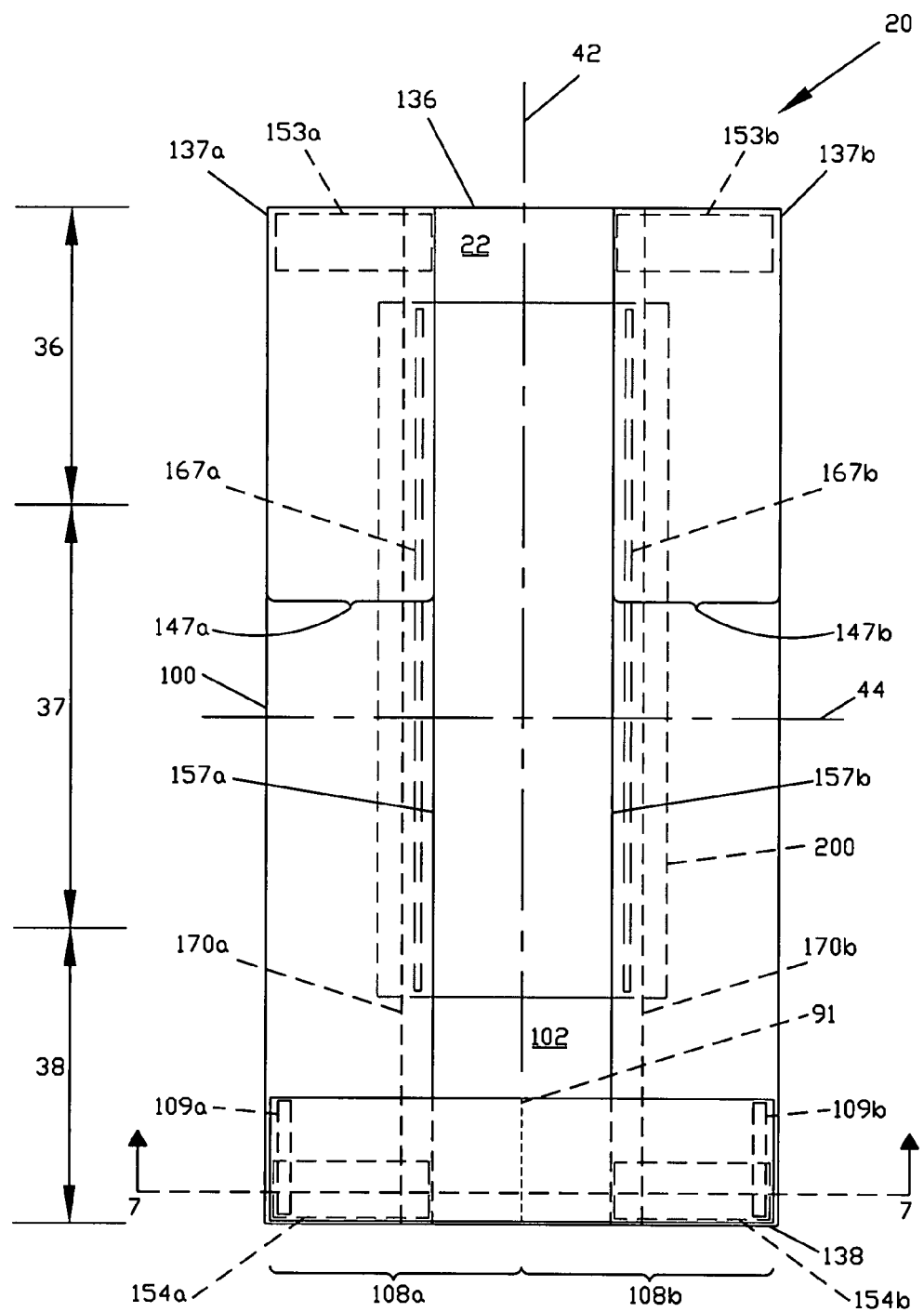
FIG. 5 is a plan view of the exemplary diaper 20 with two belt ears extending laterally. In this figure, the interior portion of the diaper 20 is shown facing the viewer.
Figure 6:
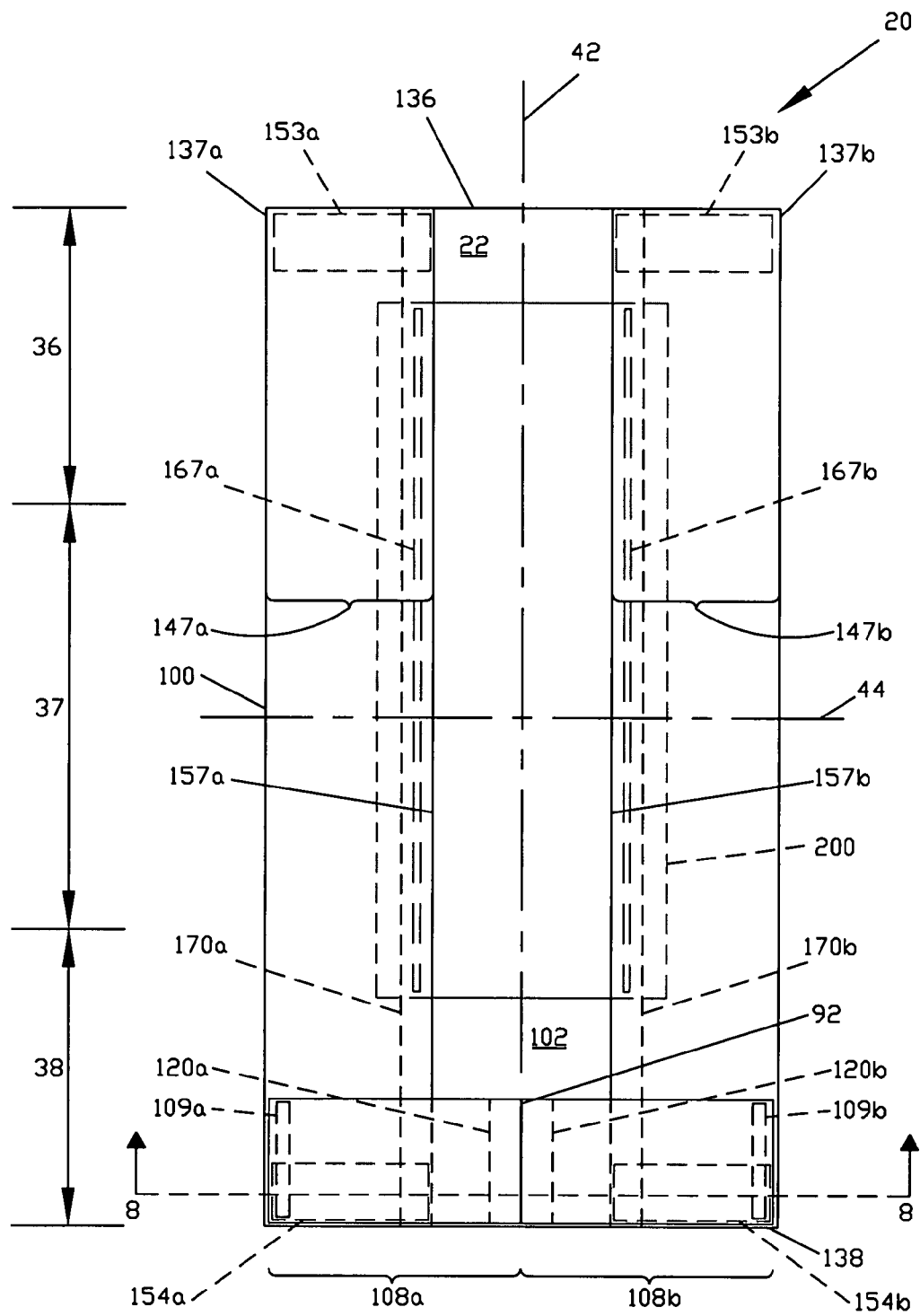
FIG. 6 is a plan view of the diaper 20 of FIG. 5 with the interior portion of the diaper 20 shown facing the viewer.
Figure 7:
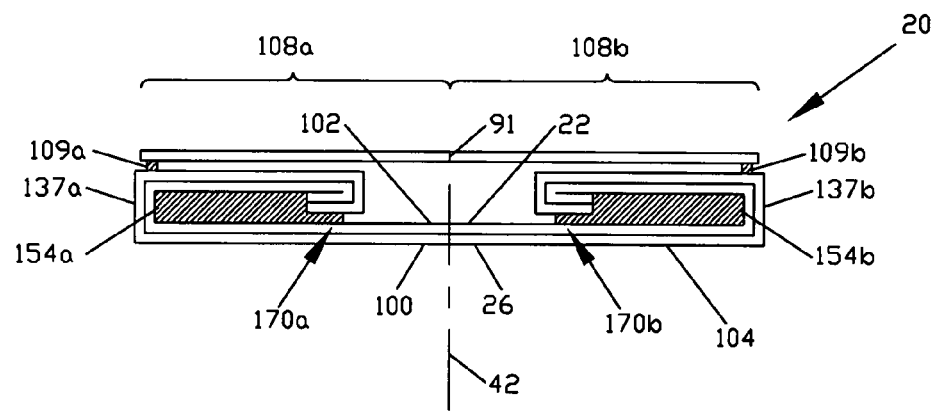
FIG. 7 is a section view of the diaper 20 of FIG. 5 taken at the section line 7-7.

Each belt ear is attached to the respective side flap 147 in an attachment zone 109, as shown in FIG. 1, FIG. 2, FIG. 4, FIG. 5, FIG. 6, FIG. 7, FIG. 8, FIG. 9, and FIG. 10. For ease of manufacturing and packaging, it is preferable that the belt ears 106 and/or 108 remain disposed laterally inward until a user desires to deploy them for use when applying the diaper 20 onto the body of a wearer. For this purpose, as shown in FIG. 5 and FIG. 7, one edge of each belt ear may be defined by a frangible line of attachment 91 along which the belt ear can be detached from the laterally opposing belt ear for deployment laterally outward in preparation for use. Such a frangible line of attachment may be formed in a layer or a laminate of layers by perforation, by the formation of a brittle area or areas at which the material will preferentially fracture when stressed, by the formation of a weaker area or areas at which the material will preferentially tear when stressed, by the formation of a friable area or areas at which the material will preferentially crumble when stressed and/or bent, or by any other method of providing frangibility that is suitable for the materials involved.

Figure 8:
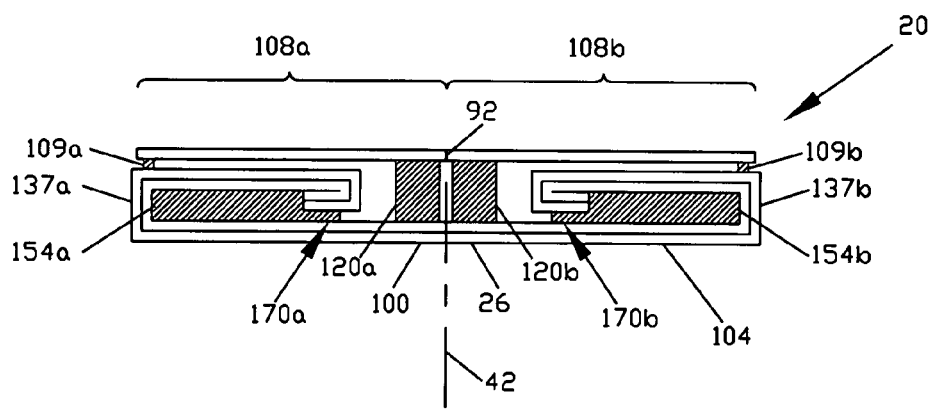
FIG. 8 is a section view of the diaper 20 of FIG. 6 taken at the section line 8-8.
Figure 9:
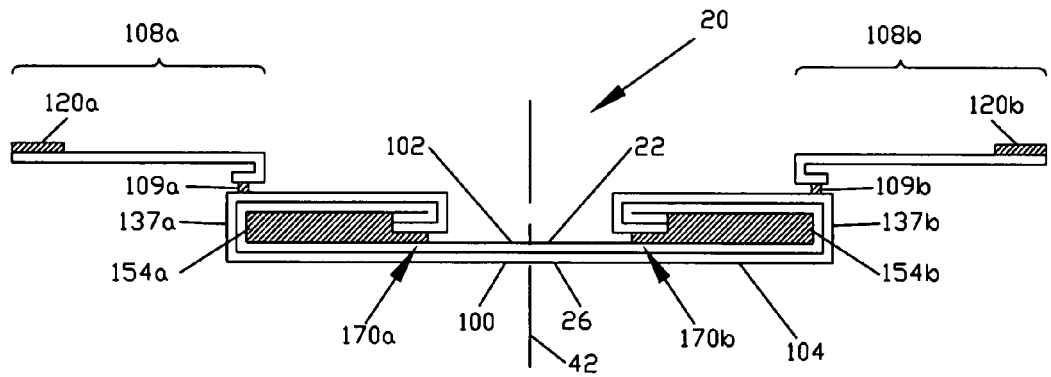
FIG. 9 is a section view of the diaper 20 of FIGS. 1 and 2 taken at the section line 9-9.
Figure 10:
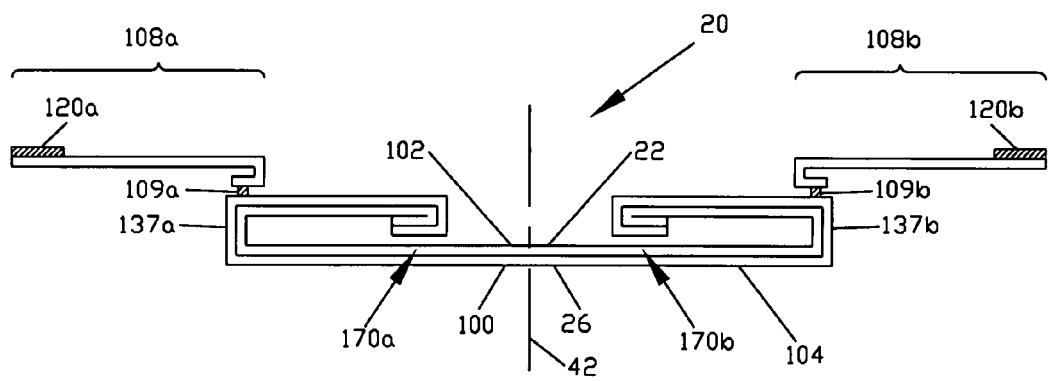
FIG. 10 is a section view of the diaper 20 of FIGS. 1 and 2 taken at the section line 10-10.

Alternatively, as shown in FIG. 6 and FIG. 8, one edge of each belt ear may be defined by a cut line 92 at which the belt ear is severed from the laterally opposing belt ear during manufacture. Because the formation of this cut line would allow the belt ear to deploy prematurely, the belt ear may be held laterally inwardly disposed by a releasable attachment member until being released and deployed laterally outward so as to project laterally outward beyond the adjacent side flap. As shown in FIG. 8, a fastening element 120 may serve to releasably attach the belt ear until it is deployed for use. Such a releasable attachment may also be used in combination with a belt ear that is defined by a frangible line of attachment 91 if additional assurance is desired that the belt ear will not inadvertently be deployed prematurely, for example by handling that might rupture the frangible line of attachment.

Portions of the diaper 20 can be fastened together to encircle the waist and the legs of the wearer in many well-known ways. For example, separate fastening devices such as safety pins, separate tapes, a separate tie strap or straps, and/or a separate belt can be used for this purpose. Alternatively or in addition, fastening elements can be incorporated into the diaper 20 to enable a user to apply the diaper to the body of the wearer without, or in conjunction with, any separate fastening devices. Many suitable types of such incorporated fastening elements are well-known, including, for example, tapes, adhesives, adhesive tape tabs, ties, buttons, hooks, loops, snap fasteners, other forms of mechanical fasteners, cohesive patches, etc. When configured for use, portions of these incorporated fastening elements may project laterally or longitudinally outward or they may lie entirely inside the edges of the diaper 20.

For example, laterally opposing fastening elements 120 may be attached to the belt ears. These fastening elements 120 may be disposed on the back belt ears 108, as shown in FIG. 1, FIG. 2, FIG. 3, FIG. 8, FIG. 9, and FIG. 10. Such fastening elements 120 may be used to fasten the back belt ears 108 to the front waist region 36 or to fasten the back belt ears 108 to front belt ears 106, if present. Fastening elements may similarly be disposed on front belt ears 106 as shown in FIG. 4 and may be used to fasten the front belt ears 106 to the back waist region 38 or to fasten the front belt ears 106 to back belt ears 108, if present. In some embodiments in which both front belt ears and back belt ears are present, fastening elements may be attached to one but not the other. In other embodiments in which both front belt ears and back belt ears are present, complementary fastening elements may be attached to the respective belt ears such that the front belt ears may be fastened to their corresponding back belt ears. Fastening elements may be disposed on a waist region not having belt ears extending from it and may be used to attach that waist region to belt ears extending from the opposing waist region. Fastening elements 120 may be disposed on both the back belt ears 108 and the front belt ears 106. Such fastening elements 120 may be used to fasten the respective left and right pairs of such ears together or to fasten the respective belt ears to the opposing waist regions.

Several configurations of cohesive fastening patches are described in U.S. Patent Application Publication No. 2005/0171499A1. In the present invention, it is preferable that such cohesive fastening patches be disposed on the belt ears. For example, in FIG. 18, FIG. 19, FIG. 20 and FIG. 21, the back fastening elements 120 may be formed by cohesive fastening patches and the complementary front fastening elements 110 in the front waist region 36 may be formed by compatible cohesive fastening patches.

Figure 22:
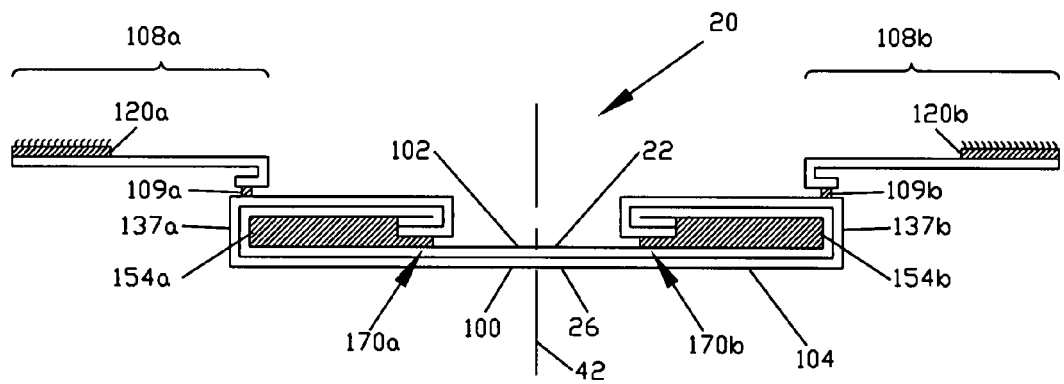
FIG. 22 is a section view of another exemplary diaper 20 taken at a section line similar to 20-20 and showing an exemplary form of fasteners.

Alternatively, when a laminate backsheet is used and is oriented with the nonwoven disposed exteriorly, some forms of mechanical fasteners that typically require specific mating fastener elements, such as hooks that typically mate with loops, may be configured to engage with the nonwoven and thereby make the inclusion of the specific mating fastener element unnecessary. For example, as shown in FIG. 22, the fastening elements 120 may be formed by hook fastening patches configured to engage with the nonwoven layer 31 of the laminate backsheet 26. Such hook fastening elements may be disposed similarly to the cohesive fastening patch fastening elements shown in FIG. 20.

In the exemplary embodiments shown in cross section in FIG. 7, FIG. 8, FIG. 9, and FIG. 10, each belt ear lies flat while laterally inwardly disposed and is folded adjacent to it attachment zone 109 where it is attached to the respective side flap 147 in order to be deployed laterally outward for use. In this configuration, the attachment zone 109 is predominately subjected to a peel force when the belt ear is subjected to a tensile force as during normal wear of the diaper 20. Therefore, it may be desirable to attach the belt ear by a through-bonding method, i.e., a bonding method that fuses the layers of material together, such as pressure bonding or thermal bonding, in order to maximize the peel strength.

Figure 12:
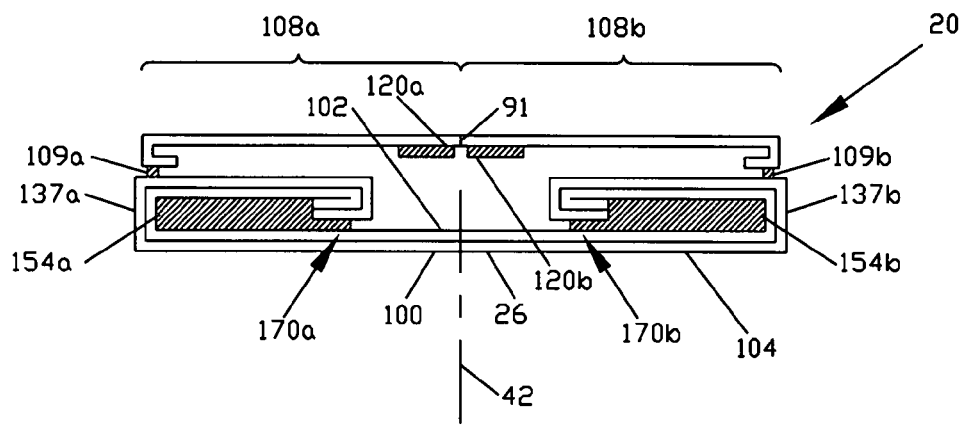
FIG. 12 is a section view of a diaper 20 showing an exemplary construction of belt ears, taken at a section line similar to 7-7.
Figure 13:
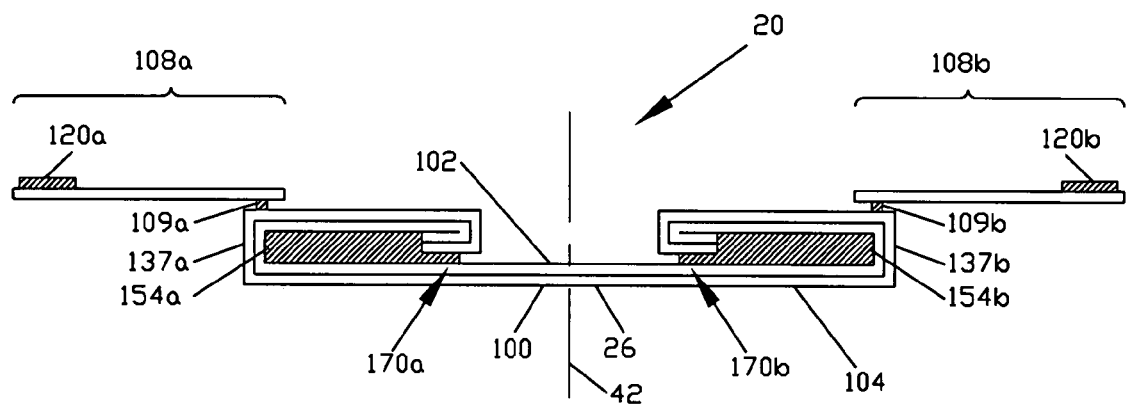
FIG. 13 is a section view of a diaper 20 showing an exemplary construction of belt ears, taken at a section line similar to 9-9.

Another exemplary attachment configuration is shown in FIG. 12 and FIG. 13, in which each belt ear is folded adjacent to its attachment zone 109 where it is attached to the respective side flap 147 while laterally inwardly disposed and is unfolded, i.e., made to lie flat, in order to be deployed laterally outward for use. In this configuration, the attachment zone 109 is predominately subjected to a shear force when the belt ear is subjected to a tensile force. Because the shear strength of an adhesive bond is often greater than its peel strength, an adhesive bond may be used to form the attachment zone 109 in this configuration, so long as suitable materials are used.

Figure 14:
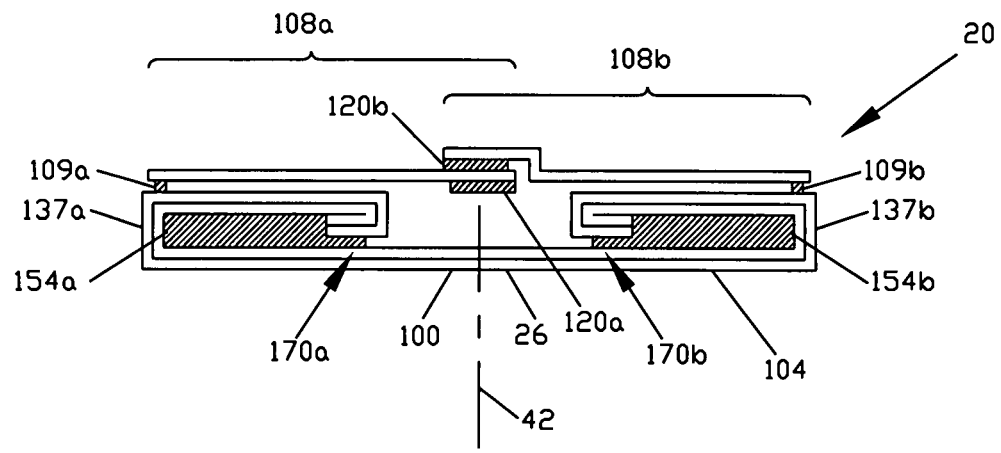
FIG. 14 is a section view of a diaper 20 showing an exemplary construction of belt ears, taken at a section line similar to 7-7.
Figure 15:
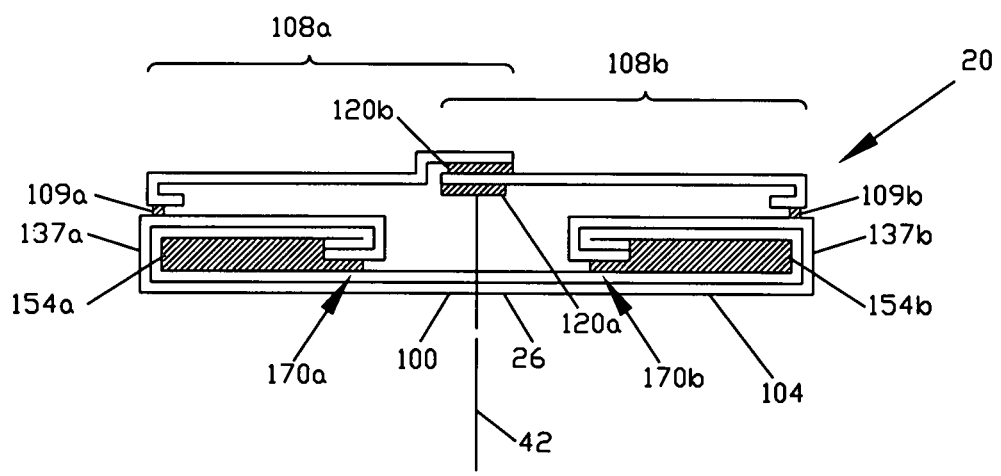
FIG. 15 is a section view of a diaper 20 showing an exemplary construction of belt ears, taken at a section line similar to 9-9.

In the exemplary embodiments shown in cross section in FIG. 7, FIG. 8, and FIG. 12, the belt ears do not overlap each other while laterally inwardly disposed. Other exemplary configurations are shown in FIG. 14 and FIG. 15, in which the belt ears overlap while in this disposition. As previously mentioned, for ease of manufacturing and packaging, it is preferable that the belt ears 106 and/or 108 remain disposed laterally inward until a user desires to deploy them for use when applying the diaper 20 onto the body of a wearer. Therefore, overlapped belt ears may be releasably attached to each other where they overlap. For example, in each of FIG. 14 and FIG. 15, a fastening element 120 serves this purpose.

The interior surface of each belt ear contacts the skin of the wearer when the diaper 20 is worn. Therefore, the layer forming the interior surface is preferably formed of a soft material that will not irritate the skin of the wearer. Many suitable materials are known in the art, including rayon and synthetic nonwovens, such as spunbonded or carded polypropylene, polyethylene, or polyester or other olefinic materials.

Figure 16:
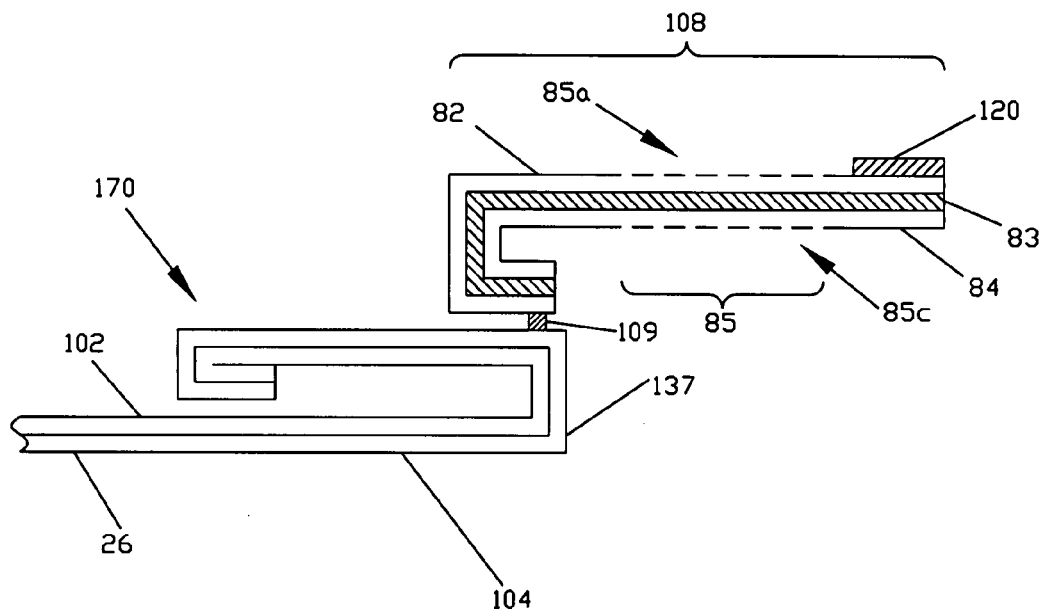
FIG. 16 is a section view of a portion of a diaper 20 showing details of the construction of a belt ear, taken at a section line similar to 9-9.
Figure 17:
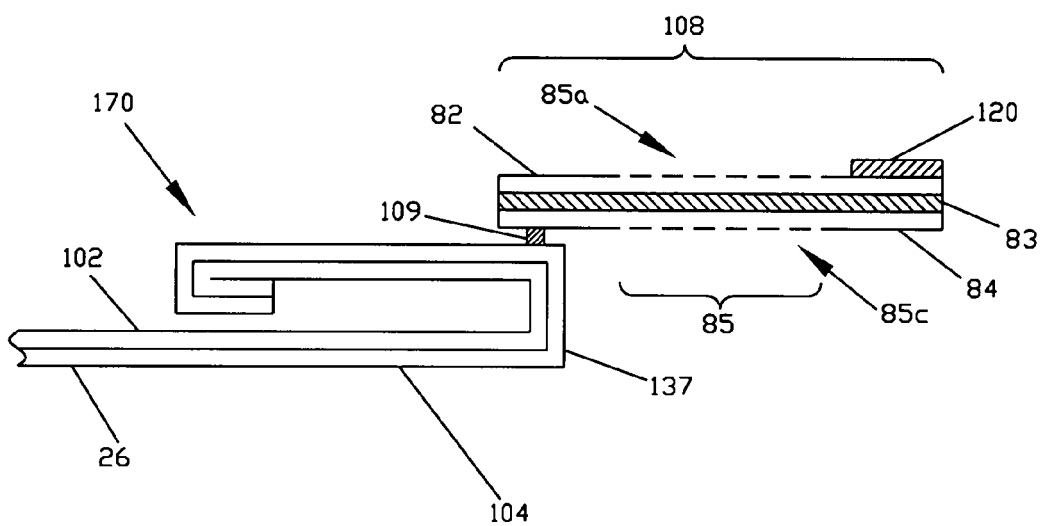
FIG. 17 is a section view of a portion of a diaper 20 showing details of the construction of a belt ear, taken at a section line similar to 9-9.
Figure 18:
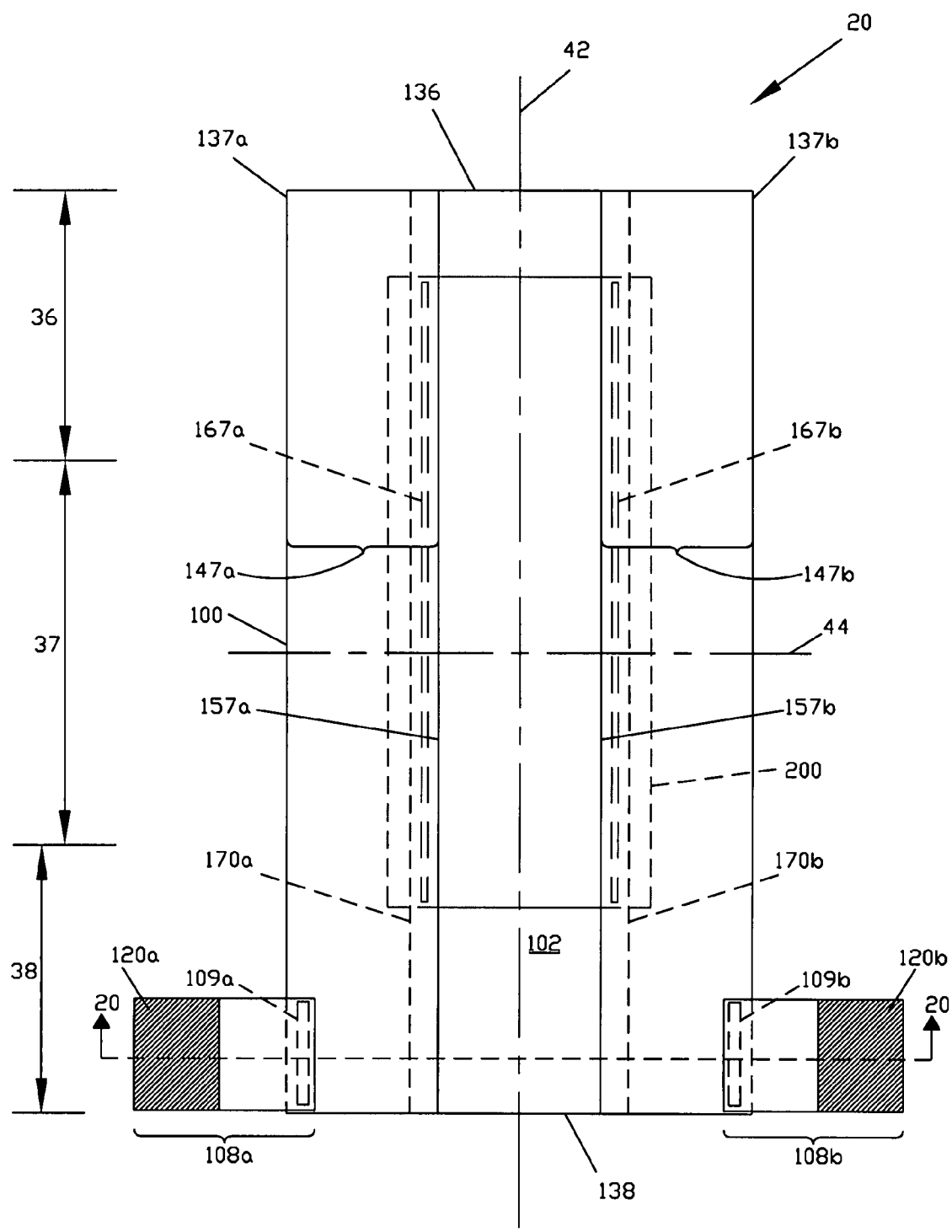
FIG. 18 is a plan view of another exemplary diaper 20 showing an exemplary form of fasteners.
Figure 19:
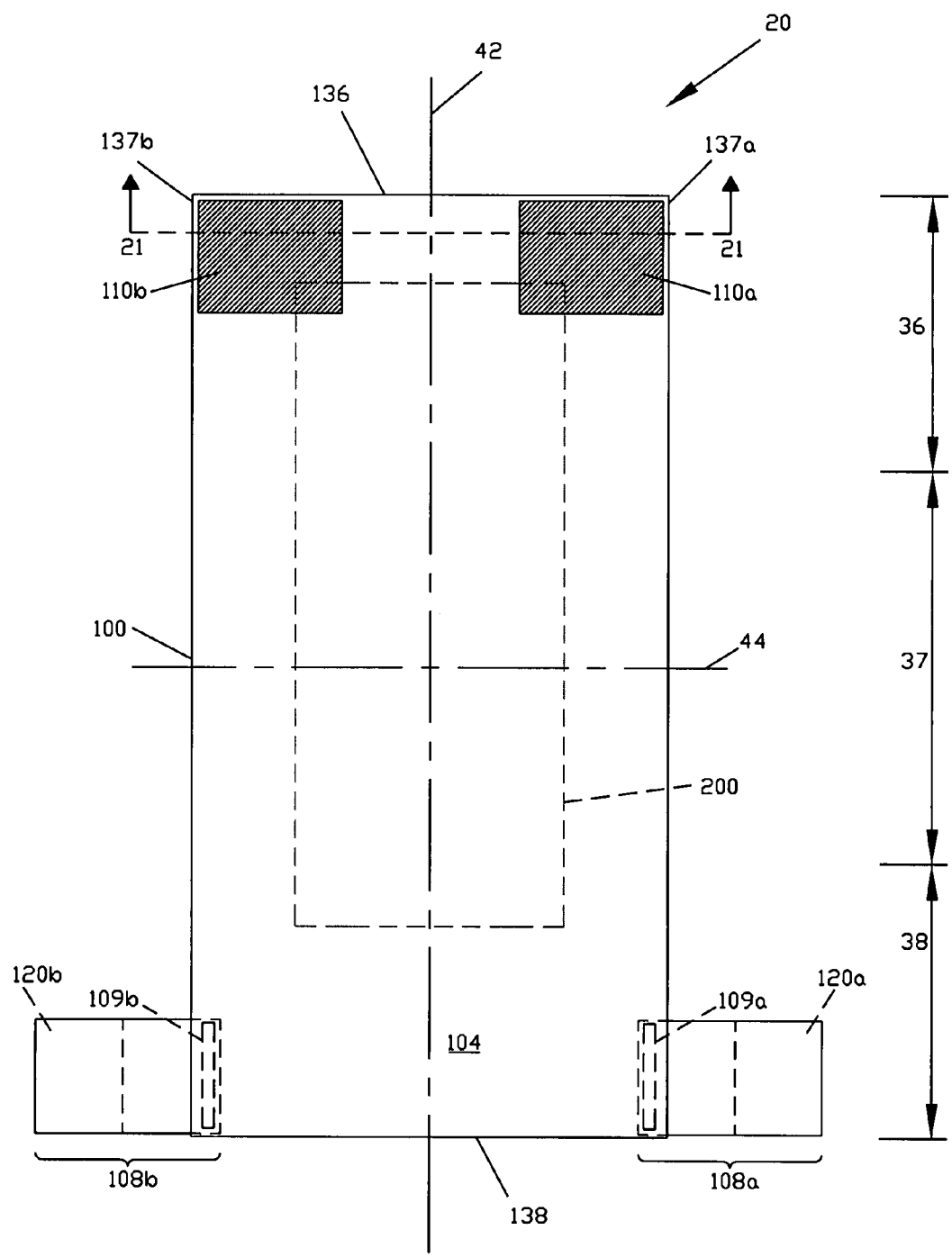
FIG. 19 is a plan view of the diaper 20 of FIG. 18 with the exterior portion of the diaper 20 shown facing the viewer.
Figure 20:
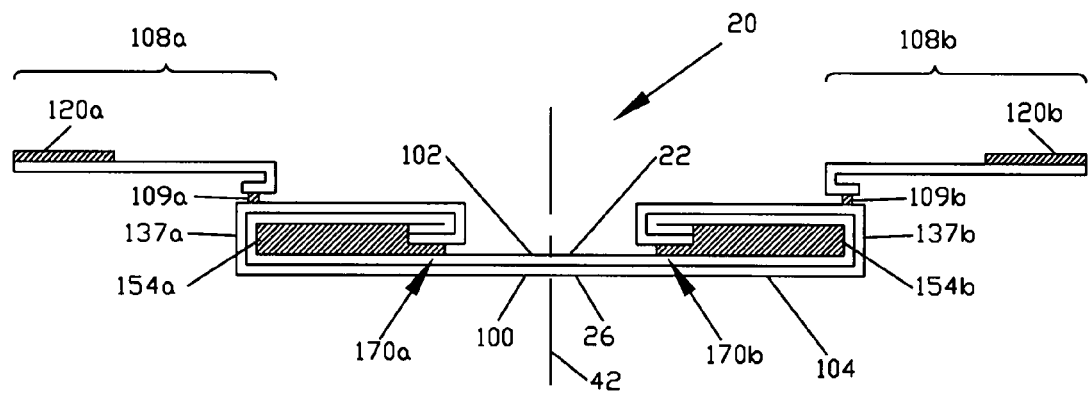
FIG. 20 is a section view of the diaper 20 of FIGS. 18 and 19 taken at the section line 20-20.
Figure 21:
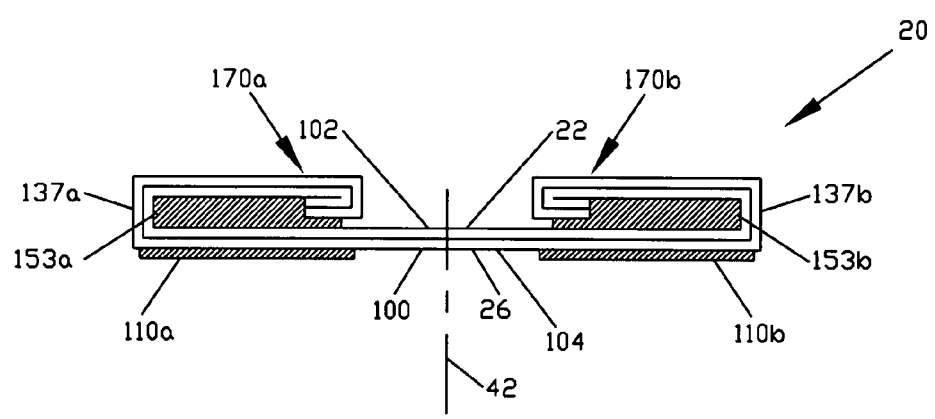
FIG. 21 is a section view of the diaper 20 of FIGS. 18 and 19 taken at the section line 21-21.

A belt ear may have a laminate structure. In particular, a belt ear may include an interior layer and an additional layer or layers disposed exteriorly of the interior layer. An elastic version of one of the aforementioned suitable materials, such as a nonwoven exhibiting substantial elastic properties, may be used for any of the layers. For example, belt ears having laminate structures are shown in FIG. 16 and FIG. 17. Each of these belt ears includes an interior skin-contacting layer 82 and an elastic layer 83 laminated to the interior layer 82. Suitable materials for the elastic layer 83 are well-known in the art, including natural rubber strands, synthetic rubber strands, elastomeric films, etc. The material chosen for the elastic layer 83 preferably exhibits a force response proportional to its elongation. Each belt ear may also include an exterior cover layer 84 laminated to the elastic layer 83 on its surface opposite the interior layer 82, thereby forming a trilaminate in which the elastic layer 83 is sandwiched between the interior layer 82 and the exterior cover layer 84.

The layers of each belt ear may be laminated by any method suitable for the elements being attached together and their constituent materials. For example, the elastic layer 83 may be maintained in a stretched condition while being attached to a relaxed skin-contacting layer 82 (and a relaxed exterior cover layer 84 if present) and then allowed to relax. The resultant contraction of the elastic layer 83 may gather the skin-contacting layer 82 in such a way as to create rugosities and the laminate thus formed may be extended in the direction of the original stretch up to the original dimension of the skin-contacting layer 82 (and the exterior cover layer 84 if present) with only the elastic layer 83 resisting the extension. A similar result may be achieved by, for example, first gathering the skin-contacting layer 82 (and the exterior cover layer 84 if present), such as by pleating it, and then attaching the elastic layer 83 in a relaxed condition. The resultant laminate may be extended in a direction perpendicular to the pleat ridges up to the original dimension of the skin-contacting layer 82 (and the exterior cover layer 84 if present) with only the elastic layer 83 resisting the extension.

In some exemplary methods, the lamination may be performed with both the elastic layer 83 and the skin-contacting layer 82 (and the exterior cover layer 84 if present) relaxed. All or a portion of the resultant laminate belt ear may subsequently be "activated" by subjecting it to elongation to create localized ruptures in a portion 85*a* of the skin-contacting layer 82 (and a portion 85*c* of the exterior cover layer 84 if present). In FIG. 16 and FIG. 17, belt ears having activation portions 85 are shown, with the ruptured portion 85*a* of the interior layer 82 and the ruptured portion 85*c* of the exterior cover layer 84 shown in dashed lines representing exemplary breaks in and/or separation of the fibers in nonwoven materials. The ruptured portion 85*a* of the interior layer 82 (and the ruptured portion 85*c* of the exterior cover layer 84 if present)

in the resultant activated portion 85 of the laminate provides little or no resistance to extension in the direction of the original elongation. For example, when a nonwoven is used for the interior layer 82 (and the exterior cover layer 84 if present), the ruptured portion(s) typically include(s) breaks in and/or separation of the fibers that render the ruptured portion(s) substantially incapable of transmitting tensile forces in the plane of the nonwoven. Some suitable activation methods are known in the art as "ring-rolling" processes.

A combination of lamination methods may be used, if desired, so long as they are suitable for the elements being attached together and their constituent materials.

As shown in FIG. 26, FIG. 27, FIG. 28, and FIG. 29, the absorbent assembly 200 includes an absorbent core 250. The absorbent core 250 has a laterally extending front edge 256, a longitudinally opposing back edge 258, a left side edge 257a, and a laterally opposing right side edge 257b. Any or all of the edges of the absorbent core 250 may lie inward of, or may coincide with, the respective edges of the absorbent assembly 200. For example, in the exemplary absorbent assembly 200 shown in FIG. 26, the side edges 257 of the absorbent core 250 are located laterally inward of the side edges 237 of the absorbent assembly 200, while the front edge 256 and back edge 258 of the absorbent core 250 coincide with the respective front edge 236 and back edge 238 of the absorbent assembly 200.

The absorbent assembly 200 may be attached to the chassis 100 over any part or the whole of the area of the absorbent assembly 200. Preferably, the absorbent assembly 200 is attached on its exterior surface 204 to the chassis 100 in a cruciform attachment pattern, i.e., in an attachment pattern that forms or is arranged in a cross or "+" shape. The cruciform attachment pattern may be contiguous, i.e., all of its portions may be touching or connected throughout the pattern in an unbroken sequence. Alternatively, the cruciform attachment pattern may include detached portions and thereby lack contiguity but still be arranged such that the shape of the overall pattern is a cruciform. For example, a discontiguous cruciform attachment pattern may include a longitudinally extending portion disposed along the longitudinal axis and separate left and right laterally distal portions disposed along or adjacent to the lateral axis and thereby form a cruciform as the shape of the overall pattern.

An exemplary contiguous cruciform attachment pattern 210 is shown in FIG. 25, FIG. 26, FIG. 27, and FIG. 28. The portions 190 of the chassis 100 that lie outside such a cruciform attachment pattern are not restrained by attachment to the absorbent assembly 200 and therefore remain extensible. In particular, a relatively narrow longitudinally extending portion 212 of a cruciform attachment pattern 210 like that shown in FIG. 25, FIG. 26, and FIG. 28 leaves the majority of the width of the chassis 100 in the front waist region 36 and in the back waist region 38 freely extensible and thereby allows extension of the chassis 100 in the lateral direction in these regions. A relatively wide laterally extending portion 214 of a cruciform attachment pattern 210 like that shown in FIG. 25, FIG. 26, and FIG. 27 prevents the portion of the chassis 100 in the crotch region 37 to which the absorbent assembly 200 is attached from shifting relative to the absorbent assembly 200 in that region. A relatively wide laterally extending portion 214 of a cruciform attachment pattern 210 may also contribute to the effectiveness of the side flaps 147 when the elastic strands 167 lift the proximal edges 157 into contact with the body of the wearer. Because the relatively wide laterally extending portion 214 of the cruciform attachment pattern 210 restrains the chassis 100 over a relatively wide portion of the width of the crotch region 37, the side flaps 147 are better supported at their bases while being lifted by the elastic strands 167

Within the extent of the cruciform attachment pattern 210, the absorbent assembly 200 may be attached to the chassis 100 continuously or intermittently. For example, a film of an adhesive material may be applied continuously over the entire area of the cruciform attachment pattern and then used to continuously attach the absorbent assembly to the chassis. As an alternative example, an adhesive material may be applied discontinuously at and inside the boundaries of the cruciform attachment pattern, such as in the form of dots, stripes, beads, spirals, etc., and then used to attach the absorbent assembly to the chassis.

The cruciform attachment pattern 210 may be disposed either symmetrically or asymmetrically with respect to either or both of the longitudinal axis 42 and the lateral axis 44 of the chassis 100. In addition, the cruciform attachment pattern 210 may be disposed symmetrically or asymmetrically with respect to either or both of the side edges 237 and the front edge 236 and the back edge 238 of the absorbent assembly 200.

Suitable configurations of cruciform attachment patterns are disclosed in U.S. Pat. No. 6,962,578 issued on 8 Nov. 2005.

The absorbent core 250 may be disposed between a lower covering sheet that is disposed on the exterior face of the absorbent core 250 in a face-to-face arrangement with the interior surface 102 of the chassis and an upper covering sheet that is disposed on the interior face of the absorbent core 250. Such an upper covering sheet and lower covering sheet may be attached together to contain the absorbent core 250 between them and thereby form the absorbent assembly 200. For example, in the exemplary absorbent assembly 200 shown in the figures, an upper covering sheet 24 and a lower covering sheet 25 are attached together at or adjacent to the side edges 237 of the absorbent assembly 200 in adhesive attachment zones 29. Alternatively, the upper covering sheet 24 and the lower covering sheet 25 may be attached together in places other than the side edges 237 of the absorbent assembly 200, e.g., at or adjacent to the end edges 236 and 238, or at or adjacent to both the end edges 236 and 238 and the side edges 237.

The upper covering sheet 24 is water-permeable and allows liquid waste to pass through to the absorbent core 250, where the liquid waste is absorbed. The lower covering sheet 25 may be water-impermeable. However, the lower covering sheet 25 preferably is water-permeable.

The absorbent core may include an acquisition component in addition to one or more storage components. The absorbent core acquisition component serves to acquire deposited liquid bodily waste material and transfer it to the absorbent core storage component. Any porous absorbent material which will imbibe and partition liquid bodily waste material to the storage component or components may be used to form the acquisition component. Preferred materials for the acquisition component include synthetic fiber materials, open celled polymeric foam materials, fibrous nonwoven materials, cellulosic nonwoven materials, and various combination synthetic/cellulosic nonwoven materials. Examples of such acquisition materials are more fully described in U.S. Pat. No. 4,950,264 issued on Aug. 21, 1990.

Figure 29:
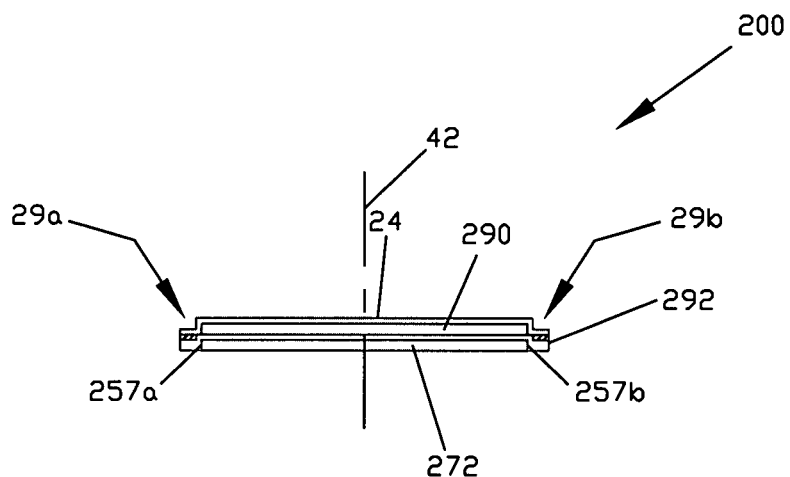
FIG. 29 is a section view of another exemplary absorbent assembly 200 taken at a section line similar to 27-27.

Such an acquisition component 290 overlying an absorbent core storage component 272 is shown in FIG. 29. A separation sheet 292 of, e.g., a tissue or a nonwoven material, may be disposed between the absorbent core storage component 272 and the absorbent core acquisition component 290 to help ensure that none of the gel formed by a superabsorbent polymer that may be included in the absorbent core storage component reaches the skin of the wearer.

Suitable well-known absorbent materials for the absorbent core include cellulose fibers in the form of comminuted wood pulp, which is commonly known as "airfelt", layers or sheets of natural or synthetic fibrous material, superabsorbent polymer, etc. These absorbent materials may be used separately or in combination and many may be used in a discrete form, i.e., in the form of fibers, granules, particles, layers and the like.

Figure 30:
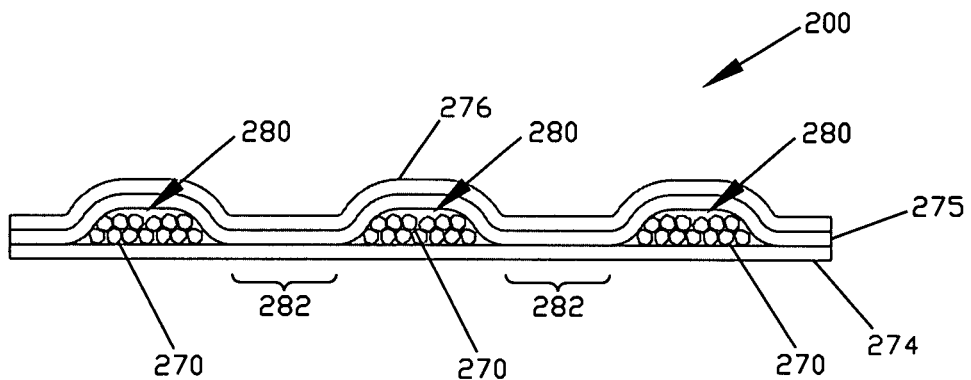
FIG. 30 is a section view of an exemplary absorbent core 250.

The discrete form of an absorbent material may be immobilized in pockets formed by a layer of a thermoplastic material, such as a hot melt adhesive, that intermittently contacts and adheres to a substrate, such as a covering sheet, while diverging away from the substrate at the pockets. Absorbent assemblies having such pocket structures are described in detail in U.S. Patent Application Publications Nos. 2004/0167486 of 26 Aug. 2004 and 2004/0162536 of 19 Aug. 2004. An exemplary absorbent assembly 200 having such a structure is shown in FIG. 30. In this absorbent assembly 200, the absorbent core 250 includes particles of superabsorbent polymer 270 that are contained inside pockets 280 formed by a layer 275 of a thermoplastic material. The layer 275 of the thermoplastic material intermittently contacts and adheres to a substrate sheet 274 at the areas of attachment 282. Between the areas of attachment 282, the layer 275 diverges away from the substrate sheet 274 to form the pockets 280. The layer 275 may have the form of a sheet of fibers of the thermoplastic material through which the liquid waste may pass to the particles of superabsorbent polymer 270 to be absorbed.

In FIG. 30, a separate thermoplastic layer covering sheet 276 is shown overlying the layer 275 of the thermoplastic material. Alternatively, the separate thermoplastic layer covering sheet may be omitted.

Statements of Incorporation by Reference and Intended Scope of Claims

The disclosures of all patents, patent applications and any patents which issue thereon, as well as any corresponding published foreign patent applications, and all publications listed and/or referenced in this description, are hereby incorporated herein by reference. It is expressly not admitted that any of the documents or any combination of the documents incorporated herein by reference teaches or discloses the present invention. To the extent that any meaning or definition of a term in this document conflicts with any meaning or definition of the same term in a document incorporated by reference, the meaning or definition assigned to that term in this document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper comprising:
a chassis comprising a front waist region including a front waist end edge, a longitudinally opposing back waist region including a back waist end edge, and a crotch region between the waist regions, a longitudinal axis and a lateral axis, laterally opposing side edges defining its width, the longitudinally opposing front and back waist end edges defining its length;
an absorbent assembly;
an interior surface and an exterior surface;
a water-impermeable backsheet;
laterally opposing side flaps formed by laterally inwardly folded portions of the chassis, each side flap being attached to the interior surface adjacent to its longitudinally distal ends and comprising a longitudinally extending elastic gathering member attached adjacent to its proximal edge, wherein the proximal edge is substantially linear between the front and back waist end edges, and wherein the proximal edge between the front and back waist end edges is substantially parallel with the longitudinal axis;
a first belt ear and a second belt ear making up a pair of laterally opposing deployable belt ears having a distal edge and a proximal edge, wherein each of the belt ears at or adjacent the distal edge are attached at or adjacent to the side edges of the chassis in the back waist region;
wherein, prior to application of the diaper to a wearer, the belt ears extend laterally inward from the side edge of the chassis and are disposed in a surface to surface orientation with an interior surface of the chassis in the back waist region;
wherein the first belt ear comprises a first fastener and wherein the second belt ear comprises a second fastener, wherein the first fastener is engaged with the interior surface of the diaper in the back waist region, and wherein the second fastener is engaged with the interior surface of the diaper in the back waist region;
wherein, prior to application of the diaper to a wearer, the belt ears do not overlap each other in the back waist region; and
wherein, when the diaper is configured to form a waist opening and a pair of leg openings, the belt ears do not overlap each other;
wherein the belt ears are formed separately from the chassis;
wherein the chassis comprises the belt ears in both of the waist regions.

2. The disposable diaper of claim 1 wherein the chassis comprising fastening elements disposed on at least two of the belt ears and adapted for fastening the front waist region to the back waist region to encircle a waist and legs of a wearer.

3. The disposable diaper of claim 2 wherein the fastening elements comprise hooks.

4. The disposable diaper of claim 1 wherein the chassis comprising a nonwoven inner liner attached to the backsheet and forming a portion of the interior surface.

5. The disposable diaper of claim 1 wherein the backsheet is a laminate of a film and a nonwoven, the nonwoven being disposed exteriorly of the film.

6. The disposable diaper of claim 5 wherein the fastening elements comprise hooks adapted to engage with the backsheet nonwoven.

7. The disposable diaper of claim 1 wherein the absorbent assembly is attached to the chassis in a cruciform pattern of attachment comprising a longitudinally extending portion intersecting a laterally extending portion.

8. The disposable diaper of claim 7 wherein a portion of the chassis underlying the absorbent assembly and lying outside the cruciform pattern is laterally extensible.

9. The disposable diaper of claim 8 wherein the extensible portion of the chassis comprises a formed web material including at least two distinct laterally extending embossed regions each containing a pattern of generally longitudinally oriented alternating ridges and valleys created by an embossment and also containing an unembossed region located between the embossed regions, such that the extensible portion of the chassis can be laterally extended to a given extent with the application of relatively less force than that required to laterally extend the same portion of the chassis to the same given extent before the embossment.

10. The disposable diaper of claim 7 wherein the longitudinally extending portion is disposed symmetrically with respect to the longitudinal axis and the laterally extending portion is disposed asymmetrically with respect to the lateral axis.

11. The disposable diaper of claim 10 wherein the laterally extending portion is longitudinally offset toward the front waist region.

12. The disposable diaper of claim 1 wherein the belt ears are separated by a frangible line.

13. The disposable diaper of claim 1 wherein the belt ears in the front and back waist regions are adapted to engage with each other.

14. The disposable diaper of claim 13 wherein the belt ears in the front waist region comprise hook—type fasteners.

15. The disposable diaper of claim 13 wherein the belt ears in the back waist region comprise hook-type fasteners.

16. The disposable diaper of claim 14 wherein the belt ears in the back waist region comprise loop-type fasteners.

17. The disposable diaper of claim 15 wherein the belt ears in the front waist region comprise loop-type fasteners.

18. The disposable diaper of claim 13 wherein the absorbent assembly comprises absorbent material immobilized in pockets.

19. The disposable diaper of claim 13 wherein the pockets are formed in part by a layer of a thermoplastic material.

* * * * *